United States Patent
Bigler et al.

(10) Patent No.: US 8,153,134 B2
(45) Date of Patent: Apr. 10, 2012

(54) ANTI-MDL-1 ANTIBODIES

(75) Inventors: Michael E. Bigler, Redwood City, CA (US); Paul G. Heyworth, San Francisco, CA (US); Joseph H. Phillips, Palo Alto, CA (US); Leonard G. Presta, San Francisco, CA (US)

(73) Assignee: Schering Corporation, Kenilworth, NJ (US)

( * ) Notice: Subject to any disclaimer, the term of this patent is extended or adjusted under 35 U.S.C. 154(b) by 106 days.

(21) Appl. No.: 12/596,896

(22) PCT Filed: Apr. 21, 2008

(86) PCT No.: PCT/US2008/005128
§ 371 (c)(1),
(2), (4) Date: Dec. 21, 2009

(87) PCT Pub. No.: WO2008/133857
PCT Pub. Date: Nov. 6, 2008

(65) Prior Publication Data
US 2010/0150945 A1  Jun. 17, 2010

Related U.S. Application Data

(60) Provisional application No. 60/913,436, filed on Apr. 23, 2007, provisional application No. 60/944,714, filed on Jun. 18, 2007.

(51) Int. Cl.
*A61K 39/395* (2006.01)
*C12P 21/08* (2006.01)
*C07K 16/00* (2006.01)

(52) U.S. Cl. ............. 424/172.1; 530/387.1; 530/387.3; 435/69.9; 435/334

(58) Field of Classification Search .......... None
See application file for complete search history.

(56) References Cited

U.S. PATENT DOCUMENTS

| 6,953,843 B2 * | 10/2005 | Bakker et al. | 530/391.3 |
| 7,319,140 B2 * | 1/2008 | Bakker et al. | 530/387.3 |
| 2005/0084900 A1 * | 4/2005 | Bakker et al. | 435/7.1 |

FOREIGN PATENT DOCUMENTS

| WO | WO 99/06557 | 2/1999 |
| WO | WO 2006/052975 | 5/2006 |

OTHER PUBLICATIONS

Bakker et al. (1999) *PNAS U.S.A.* 96(17):9792-9796 "Myeloid DAP12-associating lectin (MDL)-1 is a cell surface receptor involved in the activation of myeloid cells".
Bouchon et al. (2000) *J. Immunol.* 164:4991-4995 "Cutting Edge: Inflammatory Responses Can Be Triggered by TREM-1, a Novel Receptor Expressed on Neutrophils and Monocytes".
Campbell and Colonna (1999) *Int. J. Biochem.* Cell Biol. 31:631-636 "DAP12: a key accessory protein for relaying signals by Natural Killer cell receptors".
Davies et al. (1996) *Immunotechnology* 2(3):169-179 "Affinity improvement of single antibody VH domains: residues in all three hypervariable affect antigen binding".
Dietrich etal. (2000) *J. Immunol.* 164:9-12 "Cutting Edge: Signal-Regulatory Protein β1 Is a DAP12-Associated Activating Receptor Expressed in Myeloid Cells".
Gingras et al. (2001) *Mol. Immun.* 38:817-824 "TREM-1, MDL-1, and DAP12 expression is associated with a mature stage of myeloid development".
Holt et al. (2003) *Trends in Biotechnology* 21(11):484-490 "Domain antibodies: proteins for therapy".
Lanier and Bakker (2000) *Immunol. Today* 21(12):611-614 "The ITAM-bearing transmembrane adaptor DAP12 in lymphoid and myeloid cell function".
Lanier et al. (1998) *Nature* 391(6668):703-707 "Immunoreceptor DAP12 bearing a tyrosine-based activation motif is involved in activating NK cells".
Little et al. (2000) *Immunology Today* 21(8):364-370 "Of mice and men: hybridoma and recombinant antibodies".
Nochi et al. (2003) *Am. J. of Pathology* 162:1191-1201 "Modulation of Hepatic Granulomatous Responses by Transgene Expression of DAP12 or TREM-1-Ig Molecules".
Turnbull and Colonna (2007) *Nature Reviews Immunology* 7(2):155-161 "Activating and inhibitory functions of DAP12".

* cited by examiner

*Primary Examiner* — Cherie M Woodward
(74) *Attorney, Agent, or Firm* — Sheela Mohan-Peterson

(57) ABSTRACT

Antibodies to human MDL-1 are provided, as well as uses thereof, e.g., in treatment of immune disorders, in particular, infectious diseases and sepsis.

8 Claims, 9 Drawing Sheets

```
                       |-----CRH1-----|                           |---CDRH2---|
DX297_VH  EVQLVESGGGDLVKPGGSLKLSCTASGFAF--SNYDMSWVRQTPEKRLEWVAYISGGGGTT  58
DX230_VH  EVQLVESGGGDLVKPGGSLKLSCAASGFAF--SNYDMSWVRQTPEKRLEWVAYISGGGGTT  58
DX241_VH  DVKLVESGGGLVKPGGSLVKLGGSLKLSCAASGFTF--SSYYMSWVRQTPDKRLELVAAINSNGGTT  58
DX244_VH  QIQLVQSGPELKKPGETVKISCKASGYTF--TIYAMNWVKQAPGKGLEWMGWINTDTGEP  58
DX246_VH  QVTLKESGPGILKPSQTLSLTCSFSGFSLSTSGMNVGWIRQPSGKGLEWLAHIWWD-DDK  59

|---CDRH3---|
DX297_VH  YYSDTVKGRFTISRDNARNTLYLQMSSLKSEDTAIYYCARHPIY-----YGKPYWGQ  110
DX230_VH  YYSDTVKGRFTISRDNAKNTLYLQMSSLKSEDTAMYYCVRHAVY-----YGKPYWGQ  110
DX241_VH  YYPDTVKGRFTISRDNAKNTLYLQMSSLKPEDTALFYCVRDGEFG----HYFDYWGQ  111
DX244_VH  TYADDFKGRFAFSLETSASTAYLQINNLKNEDMATYFCARSSEVFYD---YRFDYWGQ  113
DX246_VH  YYNPSLKSQLTISKDTSRNQVFLKITSVDTADTATYYCARRAFYGSNYDYYAMDYWGQ  117

DX297_VH  GTTLTVSS  118  (SEQ ID NO: 5)
DX230_VH  GTTLTVSS  118  (SEQ ID NO: 1)
DX241_VH  GTTLTVSS  119  (SEQ ID NO: 2)
DX244_VH  GTALTVSS  121  (SEQ ID NO: 3)
DX246_VH  GTSVTVSS  125  (SEQ ID NO: 4)
```

FIGURE 1

```
              ---CDRH1---                                    ---CDRH2-
DX233_VH  EVQMQQSGAELVKPGASVKLSCTASGFNIKD--TYMHWVKQRPEQGLEWIGRIDPANGIT     58
DX239_VH  QVQLQQSGAELVRPGTSVKISCKASGYGFNN--YWLGWVKQRPGHGLEWIGDIYPGSGNT     58
DX240_VH  QVQLLQSGAELVKPGASVKISCKASGYTFTD--HAIHWVKQKPEQGLEWIGYISPGDGDI     58

------CDRH3-----
DX233_VH  KSDPKFQGKATITADTSSNTAYLQLNSLTSEDTAVYSCAPYSGNYVW-----FPYWGQ    110
DX239_VH  YYNENFKGRATLTADKSSTTAYMQVSSLTSEDSAVYFCARGKES--------FAYWGQ    108
DX240_VH  KYNEKFKDKATLTADKSSSIAYMQLNSLTSEDSAVYFCKNFDYDFI------FDFWGQ    110

DX233_VH  GTLVTVSA    118  (SEQ ID NO: 6)
DX239_VH  GTLVTVSA    116  (SEQ ID NO: 7)
DX240_VH  GTTLTVSS    118  (SEQ ID NO: 8)
```

FIGURE 2

```
                 -----CDRL1----                        -CDRL2-
DX244_VL  DIQMTQSPSSLSASLGERVSLTCRASQDIGSS----LNWLQQEPDGTIKRLIYATSNLDS 56
DX246_VL  ENVLTQSPAIMSASPGEKVTMTCSVSSSVSYI----HWYQQKSSTSPKLWIYDTSKLAS 55
DX297_VL  DIVLTQSPASLAVSLGQRATISCRASESVEHYGTSLMQWYQQKPGQPPRLLIYAASNVES 60
DX230_VL  DIVLTQSPPSLAVSLGQRATVSCRASESVEHYGTGLMQWYQQKPGQPPRLLIYAASNVES 60
DX241_VL  SIVMTQTPKFLLVSAGDRVTITCKASQSVNND----VAWYQQKPGQSPKLLIYYASNRYT 56

--CDRL3--
DX244_VL  GVPKRFSGSRSGSDYSLTISSLESEDFVHYYCLQYASSPFTFGSGTKLEIKR 108  (SEQ ID NO: 11)
DX246_VL  GVPGRFSGSGSGNSYSLTISSMEAEDVATYYCFQGSGYPLTFGAGTKLELKR 107  (SEQ ID NO: 12)
DX297_VL  GVPARFSGSGGSGTDFSLNIHPVEEDDIAMYFCQQNRKVPWTFGGGTKLEIKR 112 (SEQ ID NO: 13)
DX230_VL  GVPARFSGSGSGTDFSLNIHPVEEDDIAMYFCQQSRKVPWTFGGGTKLEIKR 112  (SEQ ID NO: 9)
DX241_VL  GVPDRFTGSGYGTDFTFTISTVQAEDLAVYFCQQDYNSPLTFGAGTKLELKR 108  (SEQ ID NO: 10)
```

FIGURE 3

```
            -----CDRL1------                          -CDRL2-
DX233_VL  DIVMTQSHKFMSTSVGDRVNITCKASQDVG------TAVAWYQRKPKPGKSPQVLIYWASTRHT  56
DX239_VL  DIVMTQSPSSLALSVGQKVTMSCKSSQSLFNFSNRNNYLAWYHQKPGQSPKLLMYFASTRES  63
DX240_VL  DIVMSQSPSSLAVSAGETVTMSCKSSQSLLNSRARKNYLAWYQQKPGQSPKLLIYWASTRES  63

--CDRL3--
DX233_VL  GVPDRFTGSGSGTDFTLTISNVQSEDLADYFCQQYRSYPLTFGAGTKLELKRA  108  (SEQ ID NO: 14)
DX239_VL  GVPDRFIGSGSGTDFTLTISSVQAEDLADYFCQQHFTTPYTFGGGTKLEIKRA  115  (SEQ ID NO: 15)
DX240_VL  GVPDRFTGSGSGTDFTLTISSVRAEDLAVYYCKQSYNL-YTFGGGTKLEIKRA  115  (SEQ ID NO: 16)
```

FIGURE 4

DX239 VL sequence

↑ = Affects CDR (Chothia et al.)   ^ = Affects CDR   Δ = Interface

VLK I

```
                10         20         30         40         50         60         70         80         90
DX239   DIVMTQSPSSLALSVGQKVTMSC KSSQSLFNFSNRNNYLA WYHQKPGQSPKLLMY FASTRES GVPDRFIGSGSGTDFTLTISSVQAEDLADYFC QQHFTTP
10                3                                                                                          2
                  ^                              ↑                 Δ                        ^                 ΔΔΔ
Z-012   DIQMTQSPSSLSASVGDRVTITC RASQSIS------SYLN WYQQKPGKAPKLLIY AASSLQS GVPSRFSGSGSGTDFTLTISSLQPEDFATYYC QQSYSTP
                                  ↑                    Δ                        ^                           ΔΔΔ
```

VLK II

```
                10         20         30         40         50         60         70         80         90
DX239   DIVMTQSPSSLALSVGQKVTMSC KSSQSLFNFSNRNNYLA WYHQKPGQSPKLLMY FASTRES GVPDRFIGSGSGTDFTLTISSVQAEDLADYFC QQHFTTP
18                3                         4                      3                                         2
                                                 ↑                 Δ                        ^                 Δ
Z-A19   DIVMTQSPLSLPVTPGEPASISC RSSQSLLHS-NGYNYLD WYLQKPGQSPQLLIY LGSNRAS GVPDRFSGSGSGTDFTLKISRVEAEDVGVYYC MQALQTP
45      111 1111 11            11                11 11111 1 11 1                            1 1             ΔΔΔ
                 ^               ↑                    Δ                        ^
```

VLK III

```
                10         20         30         40         50         60         70         80         90
DX239   DIVMTQSPSSLALSVGQKVTMSC KSSQSLFNFSNRNNYLA WYHQKPGQSPKLLMY FASTRES GVPDRFIGSGSGTDFTLTISSVQAEDLADYFC QQHFTTP
4                                           2                      3                                         2
                                                 ↑                 Δ                        ^                 Δ
Z-A27   EIVLTQSPGTLSLSPGERATLSC RASQSVSS----SYLA WYQQKPGQAPRLLIY GASSRAT GIPDRFSGSGSGTDFTLTISRLEPEDFAVYYC QQYGSSP
                                  ↑                    Δ                        ^                           ΔΔΔ
```

VLK IV

```
                10         20         30         40         50         60         70         80         90
DX239   DIVMTQSPSSLALSVGQKVTMSC KSSQSLFNFSNRNNYLA WYHQKPGQSPKLLMY FASTRES GVPDRFIGSGSGTDFTLTISSVQAEDLADYFC QQHFTTP
18                                          2                      3                                         2
                                                 ↑                 Δ                        ^                 Δ
52      1 1111 1111111111111111 11 11111 1 1 11 1                                 1 1111111111111 1111 111 1 1 1 1
Z-B3    DIVMTQSPDSLAVSLGERATINC KSSQSVLYSSNNKNYLA WYQQKPGQPPKLLIY WASTRES GVPDRFSGSGSGTDFTLTISSLQAEDVAVYYC QQYYSTP
                 ^                ↑                    Δ                        ^                           ΔΔΔ
```

DX239 VL = SEQ ID NO:15;  Z-012 = SEQ ID NO:71;
Z-A19 = SEQ ID NO:72;  Z-A27 = SEQ ID NO:73;  Z-B3 = SEQ ID NO:74

```
DX239 VH sequence        ↑ = Affects CDR (Chothia et al.)    ^ = Affects CDR    Δ = Interface VH1
              10         20       26   31          40              50                60             70            80 abc           90
DX239  QVQLQQSGAELVRPGTSVKISCKAS GYGFNNYWLG WVKQRPGHGLEWIG DIYPGSGNTYYNENFKG RATLTADKSSTTAYMQVSSLTSEDSAVYFCAR
23                                  3            4  4          2          3                                33                        4
DP-14  QVQLVQSGAEVKKPGASVKVSCKAS GYTFTSYGIS WVRQAPGQGLEWMG WISAYNGNTNYAQKLQG RVTMTDTSTSTAYMELRSLRSDDTAVYYCAR
              ^                    ↑↑           ↑Δ         ^^ Δ             ^^ ↑↑  ^                         ↑

VH3
              10         20       26   31          40              50                60             70            80 abc           90
DX239  QVQLQQSGAELVRPGTSVKISCKAS GYGFNNYWLG WVKQRPGHGLEWIG DIYPGSGNTYYNENFKG RATLTADKSSTTAYMQVSSLTSEDSAVYFCAR
15                                  3            4             2                                                                       4
DP-46  QVQLVESGGGVVQPGRSLRLSCAAS GFTFSSYAMH WVRQAPGKGLEWVA VISYDGSNKYYADSVKG RFTISRDNSKNTLYLQMNSLRAEDTAVYYCAR
              ^                    ↑↑           ↑Δ         ^^ Δ             ^^ ↑↑  ^                         ↑

VH4
              10         20       26   31          40              50                60             70            80 abc           90
DX239  QVQLQQSGAELVRPGTSVKISCKAS GYGFNNYWLG WVKQRPGHGLEWIG DIYPGSGNTYYNENFKG RATLTADKSSTTAYMQVSSLTSEDSAVYFCAR
12                                  3            4             2                 33                                                  4
DP-71  QVQLQESGPGLVKPSETLSLTCTVS GGSISSYYWS WIRQPPGKGLEWIG YIY-YSGSTNYNPSLKS RVTISVDTSKNQFSLKLSSVTAADTAVYYCAR
              ^                    ↑↑           ↑Δ         ^^ Δ             ^^ ↑↑  ^                         ↑

DX239 VH = SEQ ID NO:7; DP-14 = SEQ ID NO:75; DP-46 = SEQ ID NO:76; DP-71 = SEQ ID NO:77
```

| DX244 VL sequence | | | | ↑ = Affects CDR (Chothia et al.) | | ^ = Affects CDR | | △ = Interface |

```
                      10         20         30         40         50         60         70         80         90
VLK I
DX244    DIQMTQSPSSLSASIGERVSLTC RASQDIG------SSIN WLQQEPDGTIKRLIY ATSNLDS GVPKRFSGSRSGSDYSLTISSLESEDFVHYYC LQYASSP
18                                     3                         4
Z-012    DIQMTQSPSSLSASVGDRVTITC RASQSIS------SYIN WYQQKPGKAPKLLIY AASSLQS GVPSRFSGSGSGTDFTLTISSLQPEDFATYYC QQSYSTP
              ^                       ↑                      △                          3                   △△△
VLK II
                      10         20         30         40         50         60         70         80         90
DX244    DIQMTQSPSSLSASLGERVSLTC RASQDIG------SSLN WLQQEPDGTIKRLIY ATSNLDS GVPKRFSGSRSGSDYSLTISSLESEDFVHYYC LQYASSP
6                                      3                         4
Z-A27    DIVMTQSPLSLPVTPGEPASISC RSSQSLLHS-NGYNYLD WYLQKPGQSPQLLIY LGSNRAS GVPDRFSGSGSGTDFTLKISRVEAEDVGVYYC MQALQTP
              ^                       ↑                      △                          ^                    △△△

VLK III
                      10         20         30         40         50         60         70         80         90
DX244    DIQMTQSPSSLSASLGERVSLTC RASQDIG------SSIN WLQQEPDGTIKRLIY ATSNLDS GVPKRFSGSRSGSDYSLTISSLESEDFVHYYC LQYASSP
8                                      3                         4
Z-A19    EIVLTQSPGTLSLSPGERATLSC RASQSVSS-----SYLA WYQQKPGQAPRLLIY GASSRAT GIPDRFSGSGSGTDFTLTISRLEPEDFAVYYC QQYGSSP
              ^                       ↑                      △                          ^                 2  △△△
                                                                                                           2
VLK IV
                      10         20         30         40         50         60         70         80         90
DX244    DIQMTQSPSSLSASLGERVSLTC RASQDIG------SSLN WLQQEPDGTIKRLIY ATSNLDS GVPKRFSGSRSGSDYSLTISSLESEDFVHYYC LQYASSP
8                                      3                         4
Z-B3     DIVMTQSPDSLAVSLGERATINC KSSQSVLYSSNNKNYLA WYQQKPGQPPKLLIY WASTRES GVPDRFSGSGSGTDFTLTISSLQAEDVAVYYC QQYYSTP
              ^                       ↑                      △                          ^                 2  △△△
```

DX244 VL = SEQ ID NO:11; Z-012 = SEQ ID NO:71;
Z-A19 = SEQ ID NO:72; Z-A27 = SEQ ID NO:73; Z-B3 = SEQ ID NO:74

FIGURE 5C

DX244 VH sequence    ↑ = Affects CDR (Chothia et al.)    ^ = Affects CDR    Δ = Interface

```
VH1
              10         20      26    31         40              50          60             70         80 abc        90
DX244   QIQLVQSGPELKKPGETVKISCKAS GYTFTTIYAMN WVKQAPGKGLEWMG WINTDTGEPTYADDFKG RFAFSLETSASTAYLQINNLKNEDMATYFCAR
36                               3  4         3           3 2          2                          3 3 3             4
DP-14   QVQLVQSGAEVKKPGASVKVSCKAS GYTFTSYGIS WVRQAPGQGLEWMG WISAYNGNTNYAQKLQG RVTMTTDTSTSTAYMELRSLRSDDTAVYYCAR
                                  ^          ↑↑          ^ ^^                ΔΔ              ^^^^^↑^^↑↑             ↑

VH3
              10         20      26    31         40              50          60             70         80 abc        90
DX244   QIQLVQSGPELKKPGETVKISCKAS GYTFTFTIYAMN WVKQAPGKGLEWMG WINTDTGEPTYADDFKG RFAFSLETSASTAYLQINNLKNEDMATYFCAR
22                               3                          2          2                                            4
DP-46   QVQLVESGGGVVQPGRSLRLSCAAS GFTFSSSYAMH WVRQAPGKGLEWVA VISYDGSNKYYADSVKG RFTISRDNSKNTLYLQMNSLRAEDTAVYYCAR
                                  ^          ↑↑          ^ ^^                ΔΔ             ^^^^^↑^^↑↑              ↑

VH4
              10         20      26    31         40              50          60             70         80 abc        90
DX244   QIQLVQSGPELKKPGETVKISCKAS GYTFTFTIYAMN WVKQAPGKGLEWMG WINTDTGEPTYADDFKG RFAFSLETSASTAYLQINNLKNEDMATYFCAR
10                                                        3                                                        4
DP-71   QVQLQESGPGLVKPSETLSLTCTVS GGSISSYYWS WIRQPPGKGLEWIG YIY-YSGSTNYNPSLKS RVTISVDTSKNQFSLKLSSVTAADTAVYYCAR
                                  ^          ↑↑          ^ ^^                ΔΔ             ^^^^^↑^^↑↑              ↑
```

DX244 VH = SEQ ID NO:3; DP-14 = SEQ ID NO:75; DP-46 = SEQ ID NO:76; DP-71 = SEQ ID NO:77

FIGURE 5D

SEQUENCE LISTING

<160> NUMBER OF SEQ ID NOS: 77

<210> SEQ ID NO 1
<211> LENGTH: 118
<212> TYPE: PRT
<213> ORGANISM: Mus musculus -continued

<400> SEQUENCE: 1

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Ala Phe Ser Asn Tyr
            20                  25                  30

Asp Met Ser Trp Val Arg Gln Thr Pro Glu Lys Arg Leu Glu Trp Val
        35                  40                  45

Ala Tyr Ile Ser Gly Gly Gly Thr Thr Tyr Tyr Ser Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Val Arg His Ala Val Tyr Tyr Gly Lys Pro Tyr Trp Gly Gln Gly Thr
            100                 105                 110

Thr Leu Thr Val Ser Ser
        115

<210> SEQ ID NO 2
<211> LENGTH: 119
<212> TYPE: PRT
<213> ORGANISM: Mus musculus

<400> SEQUENCE: 2

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Tyr
            20                  25                  30

Tyr Met Ser Trp Val Arg Gln Thr Pro Asp Lys Arg Leu Glu Leu Val
        35                  40                  45

Ala Ala Ile Asn Ser Asn Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Pro Glu Asp Thr Ala Leu Phe Tyr Cys
                85                  90                  95

Val Arg Asp Gly Glu Phe Gly His Tyr Phe Asp Tyr Trp Gly Gln Gly
            100                 105                 110

Thr Thr Leu Thr Val Ser Ser
        115

<210> SEQ ID NO 3
<211> LENGTH: 121
<212> TYPE: PRT
<213> ORGANISM: Mus musculus

<400> SEQUENCE: 3

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Ile Tyr
            20                  25                  30

Ala Met Asn Trp Val Lys Gln Ala Pro Gly Lys Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

```
Leu Gln Ile Asn Asn Leu Lys Asn Glu Asp Met Ala Thr Tyr Phe Cys
                85                  90                  95

Ala Arg Ser Ser Glu Val Phe Tyr Asp Tyr Arg Phe Asp Tyr Trp Gly
            100                 105                 110

Gln Gly Thr Ala Leu Thr Val Ser Ser
        115                 120
```

<210> SEQ ID NO 4
<211> LENGTH: 125
<212> TYPE: PRT
<213> ORGANISM: Mus musculus

<400> SEQUENCE: 4

```
Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Asn Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Ala Phe Tyr Gly Ser Asn Tyr Asp Tyr Tyr Ala Met
            100                 105                 110

Asp Tyr Trp Gly Gln Gly Thr Ser Val Thr Val Ser Ser
        115                 120                 125
```

<210> SEQ ID NO 5
<211> LENGTH: 118
<212> TYPE: PRT
<213> ORGANISM: Mus musculus

<400> SEQUENCE: 5

```
Glu Val Gln Leu Val Glu Ser Gly Gly Asp Leu Val Lys Pro Gly Gly
1               5                   10                  15

Ser Leu Lys Leu Ser Cys Thr Ala Ser Gly Phe Ala Phe Ser Asn Tyr
            20                  25                  30

Asp Met Ser Trp Val Arg Gln Thr Pro Glu Lys Arg Leu Glu Trp Val
        35                  40                  45

Ala Tyr Ile Ser Gly Gly Gly Thr Thr Tyr Tyr Ser Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Lys Ser Glu Asp Thr Ala Ile Tyr Tyr Cys
                85                  90                  95

Ala Arg His Pro Ile Tyr Tyr Gly Lys Pro Tyr Trp Gly Gln Gly Thr
            100                 105                 110

Thr Leu Thr Val Ser Ser
        115
```

<210> SEQ ID NO 6
<211> LENGTH: 119
<212> TYPE: PRT
<213> ORGANISM: Mus musculus

```
<400> SEQUENCE: 6

Glu Val Gln Met Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Ile Thr Lys Ser Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Asn Ser Leu Thr Ser Glu Asp Thr Ala Val Tyr Ser Cys
                85                  90                  95

Ala Pro Tyr Ser Gly Asn Tyr Val Trp Phe Pro Tyr Trp Gly Gln Gly
            100                 105                 110

Thr Leu Val Thr Val Ser Ala
        115

<210> SEQ ID NO 7
<211> LENGTH: 116
<212> TYPE: PRT
<213> ORGANISM: Mus musculus

<400> SEQUENCE: 7

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Gly Phe Asn Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Ser Gly Asn Thr Tyr Tyr Asn Glu Asn Phe
    50                  55                  60

Lys Gly Arg Ala Thr Leu Thr Ala Asp Lys Ser Ser Thr Thr Ala Tyr
65                  70                  75                  80

Met Gln Val Ser Ser Leu Thr Ser Glu Asp Ser Ala Val Tyr Phe Cys
                85                  90                  95

Ala Arg Gly Lys Glu Ser Phe Ala Tyr Trp Gly Gln Gly Thr Leu Val
            100                 105                 110

Thr Val Ser Ala
        115

<210> SEQ ID NO 8
<211> LENGTH: 118
<212> TYPE: PRT
<213> ORGANISM: Mus musculus

<400> SEQUENCE: 8

Gln Val Gln Leu Leu Gln Ser Gly Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Ile Ser Pro Gly Asp Gly Asp Ile Lys Tyr Asn Glu Lys Phe
    50                  55                  60

Lys Asp Lys Ala Thr Leu Thr Ala Asp Lys Ser Ser Ser Ile Ala Tyr
65                  70                  75                  80
```

```
Met Gln Leu Asn Ser Leu Thr Ser Glu Asp Ser Ala Val Tyr Phe Cys
                85                  90                  95

Lys Asn Phe Asp Tyr Asp Phe Ile Phe Asp Phe Trp Gly Gln Gly Thr
            100                 105                 110

Thr Leu Thr Val Ser Ser
            115

<210> SEQ ID NO 9
<211> LENGTH: 112
<212> TYPE: PRT
<213> ORGANISM: Mus musculus

<400> SEQUENCE: 9

Asp Ile Val Leu Thr Gln Ser Pro Pro Ser Leu Ala Val Ser Leu Gly
1               5                   10                  15

Gln Arg Ala Thr Val Ser Cys Arg Ala Ser Glu Ser Val Glu His Tyr
            20                  25                  30

Gly Thr Gly Leu Met Gln Trp Tyr Gln Gln Lys Pro Gly Gln Pro Pro
        35                  40                  45

Arg Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Trp Thr Phe Gly Gly Gly Thr Lys Leu Glu Ile Lys Arg
            100                 105                 110

<210> SEQ ID NO 10
<211> LENGTH: 108
<212> TYPE: PRT
<213> ORGANISM: Mus musculus

<400> SEQUENCE: 10

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Asn Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Asn Ser Pro Leu
                85                  90                  95

Thr Phe Gly Ala Gly Thr Lys Leu Glu Leu Lys Arg
            100                 105

<210> SEQ ID NO 11
<211> LENGTH: 108
<212> TYPE: PRT
<213> ORGANISM: Mus musculus

<400> SEQUENCE: 11

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
```

```
                  20                  25                  30
Leu Asn Trp Leu Gln Gln Glu Pro Asp Gly Thr Ile Lys Arg Leu Ile
            35                  40                  45

Tyr Ala Thr Ser Asn Leu Asp Ser Gly Val Pro Lys Arg Phe Ser Gly
        50                  55                  60

Ser Arg Ser Gly Ser Asp Tyr Ser Leu Thr Ile Ser Ser Leu Glu Ser
65                  70                  75                  80

Glu Asp Phe Val His Tyr Tyr Cys Leu Gln Tyr Ala Ser Ser Pro Phe
                85                  90                  95

Thr Phe Gly Ser Gly Thr Lys Leu Glu Ile Lys Arg
            100                 105

<210> SEQ ID NO 12
<211> LENGTH: 107
<212> TYPE: PRT
<213> ORGANISM: Mus musculus

<400> SEQUENCE: 12

Glu Asn Val Leu Thr Gln Ser Pro Ala Ile Met Ser Ala Ser Pro Gly
1               5                   10                  15

Glu Lys Val Thr Met Thr Cys Ser Val Ser Ser Ser Val Ser Tyr Ile
                20                  25                  30

His Trp Tyr Gln Gln Lys Ser Thr Ser Pro Lys Leu Trp Ile Tyr
            35                  40                  45

Asp Thr Ser Lys Leu Ala Ser Gly Val Pro Gly Arg Phe Ser Gly Ser
        50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Ala Gly Thr Lys Leu Glu Leu Lys Arg
            100                 105

<210> SEQ ID NO 13
<211> LENGTH: 112
<212> TYPE: PRT
<213> ORGANISM: Mus musculus

<400> SEQUENCE: 13

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu His Tyr
                20                  25                  30

Gly Thr Ser Leu Met Gln Trp Tyr Gln Gln Lys Pro Gly Gln Pro Pro
            35                  40                  45

Arg Leu Leu Ile Tyr Ala Ala Ser Asn Val Glu Ser Gly Val Pro Ala
        50                  55                  60

Arg Phe Ser Gly Gly Gly Ser Gly Thr Asp Phe Ser Leu Asn Ile His
65                  70                  75                  80

Pro Val Glu Glu Asp Asp Ile Ala Met Tyr Phe Cys Gln Gln Asn Arg
                85                  90                  95

Lys Val Pro Trp Thr Phe Gly Gly Gly Thr Lys Leu Glu Ile Lys Arg
            100                 105                 110

<210> SEQ ID NO 14
<211> LENGTH: 109
<212> TYPE: PRT
<213> ORGANISM: Mus musculus
```

<400> SEQUENCE: 14

Asp Ile Val Met Thr Gln Ser His Lys Phe Met Ser Thr Ser Val Gly
1               5                   10                  15

Asp Arg Val Asn Ile Thr Cys Lys Ala Ser Gln Asp Val Gly Thr Ala
            20                  25                  30

Val Ala Trp Tyr Gln Arg Lys Pro Gly Lys Ser Pro Gln Val Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Arg Ser Tyr Pro Leu
                85                  90                  95

Thr Phe Gly Ala Gly Thr Lys Leu Glu Leu Lys Arg Ala
            100                 105

<210> SEQ ID NO 15
<211> LENGTH: 115
<212> TYPE: PRT
<213> ORGANISM: Mus musculus

<400> SEQUENCE: 15

Asp Ile Val Met Thr Gln Ser Pro Ser Ser Leu Ala Leu Ser Val Gly
1               5                   10                  15

Gln Lys Val Thr Met Ser Cys Lys Ser Gln Ser Leu Phe Asn Phe
            20                  25                  30

Ser Asn Arg Asn Asn Tyr Leu Ala Trp Tyr His Gln Lys Pro Gly Gln
        35                  40                  45

Ser Pro Lys Leu Leu Met Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Phe Thr Thr Pro Tyr Thr Phe Gly Gly Gly Thr Lys Leu Glu Ile
            100                 105                 110

Lys Arg Ala
        115

<210> SEQ ID NO 16
<211> LENGTH: 114
<212> TYPE: PRT
<213> ORGANISM: Mus musculus

<400> SEQUENCE: 16

Asp Ile Val Met Ser Gln Ser Pro Ser Ser Leu Ala Val Ser Ala Gly
1               5                   10                  15

Glu Thr Val Thr Met Ser Cys Lys Ser Gln Ser Leu Leu Asn Ser
            20                  25                  30

Arg Ala Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Arg Ala Glu Asp Leu Ala Val Tyr Tyr Cys Lys Gln

```
                    85                  90                  95
Ser Tyr Asn Leu Tyr Thr Phe Gly Gly Gly Thr Lys Leu Glu Ile Lys
            100                 105                 110

Arg Ala

<210> SEQ ID NO 17
<211> LENGTH: 10
<212> TYPE: PRT
<213> ORGANISM: Mus musculus

<400> SEQUENCE: 17

Gly Phe Ala Phe Ser Asn Tyr Asp Met Ser
1               5                   10

<210> SEQ ID NO 18
<211> LENGTH: 10
<212> TYPE: PRT
<213> ORGANISM: Mus musculus

<400> SEQUENCE: 18

Gly Phe Thr Phe Ser Ser Tyr Tyr Met Ser
1               5                   10

<210> SEQ ID NO 19
<211> LENGTH: 10
<212> TYPE: PRT
<213> ORGANISM: Mus musculus

<400> SEQUENCE: 19

Gly Tyr Thr Phe Thr Ile Tyr Ala Met Asn
1               5                   10

<210> SEQ ID NO 20
<211> LENGTH: 12
<212> TYPE: PRT
<213> ORGANISM: Mus musculus

<400> SEQUENCE: 20

Gly Phe Ser Leu Ser Thr Ser Gly Met Asn Val Gly
1               5                   10

<210> SEQ ID NO 21
<211> LENGTH: 10
<212> TYPE: PRT
<213> ORGANISM: Mus musculus

<400> SEQUENCE: 21

Gly Phe Ala Phe Ser Asn Tyr Asp Met Ser
1               5                   10

<210> SEQ ID NO 22
<211> LENGTH: 10
<212> TYPE: PRT
<213> ORGANISM: Mus musculus

<400> SEQUENCE: 22

Gly Phe Asn Ile Lys Asp Thr Tyr Met His
1               5                   10

<210> SEQ ID NO 23
<211> LENGTH: 10
<212> TYPE: PRT
<213> ORGANISM: Mus musculus

<400> SEQUENCE: 23
```

```
Gly Tyr Gly Phe Asn Asn Tyr Trp Leu Gly
1               5                   10
```

<210> SEQ ID NO 24
<211> LENGTH: 10
<212> TYPE: PRT
<213> ORGANISM: Mus musculus

<400> SEQUENCE: 24

```
Gly Tyr Thr Phe Thr Asp His Ala Ile His
1               5                   10
```

<210> SEQ ID NO 25
<211> LENGTH: 17
<212> TYPE: PRT
<213> ORGANISM: Mus musculus

<400> SEQUENCE: 25

```
Tyr Ile Ser Gly Gly Gly Gly Thr Thr Tyr Tyr Ser Asp Thr Val Lys
1               5                   10                  15

Gly
```

<210> SEQ ID NO 26
<211> LENGTH: 17
<212> TYPE: PRT
<213> ORGANISM: Mus musculus

<400> SEQUENCE: 26

```
Ala Ile Asn Ser Asn Gly Gly Thr Thr Tyr Tyr Pro Asp Thr Val Lys
1               5                   10                  15

Gly
```

<210> SEQ ID NO 27
<211> LENGTH: 17
<212> TYPE: PRT
<213> ORGANISM: Mus musculus

<400> SEQUENCE: 27

```
Trp Ile Asn Thr Asp Thr Gly Glu Pro Thr Tyr Ala Asp Asp Phe Lys
1               5                   10                  15

Gly
```

<210> SEQ ID NO 28
<211> LENGTH: 16
<212> TYPE: PRT
<213> ORGANISM: Mus musculus

<400> SEQUENCE: 28

```
His Ile Trp Trp Asp Asp Asp Lys Tyr Tyr Asn Pro Ser Leu Lys Ser
1               5                   10                  15
```

<210> SEQ ID NO 29
<211> LENGTH: 17
<212> TYPE: PRT
<213> ORGANISM: Mus musculus

<400> SEQUENCE: 29

```
Tyr Ile Ser Gly Gly Gly Gly Thr Thr Tyr Tyr Ser Asp Thr Val Lys
1               5                   10                  15

Gly
```

<210> SEQ ID NO 30

```
<211> LENGTH: 17
<212> TYPE: PRT
<213> ORGANISM: Mus musculus

<400> SEQUENCE: 30

Arg Ile Asp Pro Ala Asn Gly Ile Thr Lys Ser Asp Pro Lys Phe Gln
1               5                   10                  15

Gly

<210> SEQ ID NO 31
<211> LENGTH: 17
<212> TYPE: PRT
<213> ORGANISM: Mus musculus

<400> SEQUENCE: 31

Asp Ile Tyr Pro Gly Ser Gly Asn Thr Tyr Tyr Asn Glu Asn Phe Lys
1               5                   10                  15

Gly

<210> SEQ ID NO 32
<211> LENGTH: 17
<212> TYPE: PRT
<213> ORGANISM: Mus musculus

<400> SEQUENCE: 32

Tyr Ile Ser Pro Gly Asp Gly Asp Ile Lys Tyr Asn Glu Lys Phe Lys
1               5                   10                  15

Asp

<210> SEQ ID NO 33
<211> LENGTH: 9
<212> TYPE: PRT
<213> ORGANISM: Mus musculus

<400> SEQUENCE: 33

His Ala Val Tyr Tyr Gly Lys Pro Tyr
1               5

<210> SEQ ID NO 34
<211> LENGTH: 10
<212> TYPE: PRT
<213> ORGANISM: Mus musculus

<400> SEQUENCE: 34

Asp Gly Glu Phe Gly His Tyr Phe Asp Tyr
1               5                   10

<210> SEQ ID NO 35
<211> LENGTH: 12
<212> TYPE: PRT
<213> ORGANISM: Mus musculus

<400> SEQUENCE: 35

Ser Ser Glu Val Phe Tyr Asp Tyr Arg Phe Asp Tyr
1               5                   10

<210> SEQ ID NO 36
<211> LENGTH: 15
<212> TYPE: PRT
<213> ORGANISM: Mus musculus

<400> SEQUENCE: 36

Arg Ala Phe Tyr Gly Ser Asn Tyr Asp Tyr Tyr Ala Met Asp Tyr
1               5                   10                  15
```

```
<210> SEQ ID NO 37
<211> LENGTH: 9
<212> TYPE: PRT
<213> ORGANISM: Mus musculus

<400> SEQUENCE: 37

His Pro Ile Tyr Tyr Gly Lys Pro Tyr
1               5

<210> SEQ ID NO 38
<211> LENGTH: 10
<212> TYPE: PRT
<213> ORGANISM: Mus musculus

<400> SEQUENCE: 38

Tyr Ser Gly Asn Tyr Val Trp Phe Pro Tyr
1               5                   10

<210> SEQ ID NO 39
<211> LENGTH: 7
<212> TYPE: PRT
<213> ORGANISM: Mus musculus

<400> SEQUENCE: 39

Gly Lys Glu Ser Phe Ala Tyr
1               5

<210> SEQ ID NO 40
<211> LENGTH: 9
<212> TYPE: PRT
<213> ORGANISM: Mus musculus

<400> SEQUENCE: 40

Phe Asp Tyr Asp Phe Ile Phe Asp Phe
1               5

<210> SEQ ID NO 41
<211> LENGTH: 15
<212> TYPE: PRT
<213> ORGANISM: Mus musculus

<400> SEQUENCE: 41

Arg Ala Ser Glu Ser Val Glu His Tyr Gly Thr Gly Leu Met Gln
1               5                   10                  15

<210> SEQ ID NO 42
<211> LENGTH: 11
<212> TYPE: PRT
<213> ORGANISM: Mus musculus

<400> SEQUENCE: 42

Lys Ala Ser Gln Ser Val Asn Asn Asp Val Ala
1               5                   10

<210> SEQ ID NO 43
<211> LENGTH: 11
<212> TYPE: PRT
<213> ORGANISM: Mus musculus

<400> SEQUENCE: 43

Arg Ala Ser Gln Asp Ile Gly Ser Ser Leu Asn
1               5                   10

<210> SEQ ID NO 44
```

```
<211> LENGTH: 10
<212> TYPE: PRT
<213> ORGANISM: Mus musculus

<400> SEQUENCE: 44

Ser Val Ser Ser Val Ser Tyr Ile His
1               5                   10

<210> SEQ ID NO 45
<211> LENGTH: 15
<212> TYPE: PRT
<213> ORGANISM: Mus musculus

<400> SEQUENCE: 45

Arg Ala Ser Glu Ser Val Glu His Tyr Gly Thr Ser Leu Met Gln
1               5                   10                  15

<210> SEQ ID NO 46
<211> LENGTH: 11
<212> TYPE: PRT
<213> ORGANISM: Mus musculus

<400> SEQUENCE: 46

Lys Ala Ser Gln Asp Val Gly Thr Ala Val Ala
1               5                   10

<210> SEQ ID NO 47
<211> LENGTH: 17
<212> TYPE: PRT
<213> ORGANISM: Mus musculus

<400> SEQUENCE: 47

Lys Ser Ser Gln Ser Leu Phe Asn Phe Ser Asn Arg Asn Asn Tyr Leu
1               5                   10                  15
Ala

<210> SEQ ID NO 48
<211> LENGTH: 17
<212> TYPE: PRT
<213> ORGANISM: Mus musculus

<400> SEQUENCE: 48

Lys Ser Ser Gln Ser Leu Leu Asn Ser Arg Ala Arg Lys Asn Tyr Leu
1               5                   10                  15
Ala

<210> SEQ ID NO 49
<211> LENGTH: 7
<212> TYPE: PRT
<213> ORGANISM: Mus musculus

<400> SEQUENCE: 49

Ala Ala Ser Asn Val Glu Ser
1               5

<210> SEQ ID NO 50
<211> LENGTH: 7
<212> TYPE: PRT
<213> ORGANISM: Mus musculus

<400> SEQUENCE: 50

Tyr Ala Ser Asn Arg Tyr Thr
1               5
```

```
<210> SEQ ID NO 51
<211> LENGTH: 7
<212> TYPE: PRT
<213> ORGANISM: Mus musculus

<400> SEQUENCE: 51

Ala Thr Ser Asn Leu Asp Ser
1               5

<210> SEQ ID NO 52
<211> LENGTH: 7
<212> TYPE: PRT
<213> ORGANISM: Mus musculus

<400> SEQUENCE: 52

Asp Thr Ser Lys Leu Ala Ser
1               5

<210> SEQ ID NO 53
<211> LENGTH: 7
<212> TYPE: PRT
<213> ORGANISM: Mus musculus

<400> SEQUENCE: 53

Ala Ala Ser Asn Val Glu Ser
1               5

<210> SEQ ID NO 54
<211> LENGTH: 7
<212> TYPE: PRT
<213> ORGANISM: Mus musculus

<400> SEQUENCE: 54

Trp Ala Ser Thr Arg His Thr
1               5

<210> SEQ ID NO 55
<211> LENGTH: 7
<212> TYPE: PRT
<213> ORGANISM: Mus musculus

<400> SEQUENCE: 55

Phe Ala Ser Thr Arg Glu Ser
1               5

<210> SEQ ID NO 56
<211> LENGTH: 7
<212> TYPE: PRT
<213> ORGANISM: Mus musculus

<400> SEQUENCE: 56

Trp Ala Ser Thr Arg Glu Ser
1               5

<210> SEQ ID NO 57
<211> LENGTH: 9
<212> TYPE: PRT
<213> ORGANISM: Mus musculus

<400> SEQUENCE: 57

Gln Gln Ser Arg Lys Val Pro Trp Thr
1               5

<210> SEQ ID NO 58
<211> LENGTH: 9
<212> TYPE: PRT
```

```
<213> ORGANISM: Mus musculus

<400> SEQUENCE: 58

Gln Gln Asp Tyr Asn Ser Pro Leu Thr
1               5

<210> SEQ ID NO 59
<211> LENGTH: 9
<212> TYPE: PRT
<213> ORGANISM: Mus musculus

<400> SEQUENCE: 59

Leu Gln Tyr Ala Ser Ser Pro Phe Thr
1               5

<210> SEQ ID NO 60
<211> LENGTH: 9
<212> TYPE: PRT
<213> ORGANISM: Mus musculus

<400> SEQUENCE: 60

Phe Gln Gly Ser Gly Tyr Pro Leu Thr
1               5

<210> SEQ ID NO 61
<211> LENGTH: 9
<212> TYPE: PRT
<213> ORGANISM: Mus musculus

<400> SEQUENCE: 61

Gln Gln Asn Arg Lys Val Pro Trp Thr
1               5

<210> SEQ ID NO 62
<211> LENGTH: 9
<212> TYPE: PRT
<213> ORGANISM: Mus musculus

<400> SEQUENCE: 62

Gln Gln Tyr Arg Ser Tyr Pro Leu Thr
1               5

<210> SEQ ID NO 63
<211> LENGTH: 9
<212> TYPE: PRT
<213> ORGANISM: Mus musculus

<400> SEQUENCE: 63

Gln Gln His Phe Thr Thr Pro Tyr Thr
1               5

<210> SEQ ID NO 64
<211> LENGTH: 8
<212> TYPE: PRT
<213> ORGANISM: Mus musculus

<400> SEQUENCE: 64

Lys Gln Ser Tyr Asn Leu Tyr Thr
1               5

<210> SEQ ID NO 65
<211> LENGTH: 188
<212> TYPE: PRT
<213> ORGANISM: Homo sapiens

<400> SEQUENCE: 65
```

Met Asn Trp His Met Ile Ile Ser Gly Leu Ile Val Val Leu Lys
1               5                   10                  15

Val Val Gly Met Thr Leu Phe Leu Leu Tyr Phe Pro Gln Ile Phe Asn
            20                  25                  30

Lys Ser Asn Asp Gly Phe Thr Thr Thr Arg Ser Tyr Gly Thr Val Ser
        35                  40                  45

Gln Ile Phe Gly Ser Ser Pro Ser Pro Asn Gly Phe Ile Thr Thr
    50                  55                  60

Arg Ser Tyr Gly Thr Val Cys Pro Lys Asp Trp Glu Phe Tyr Gln Ala
65                  70                  75                  80

Arg Cys Phe Phe Leu Ser Thr Ser Glu Ser Trp Asn Glu Ser Arg
                85                  90                  95

Asp Phe Cys Lys Gly Lys Gly Ser Thr Leu Ala Ile Val Asn Thr Pro
            100                 105                 110

Glu Lys Leu Lys Phe Leu Gln Asp Ile Thr Asp Ala Glu Lys Tyr Phe
            115                 120                 125

Ile Gly Leu Ile Tyr His Arg Glu Glu Lys Arg Trp Arg Trp Ile Asn
            130                 135                 140

Asn Ser Val Phe Asn Gly Asn Val Thr Asn Gln Asn Gln Asn Phe Asn
145                 150                 155                 160

Cys Ala Thr Ile Gly Leu Thr Lys Thr Phe Asp Ala Ala Ser Cys Asp
                165                 170                 175

Ile Ser Tyr Arg Arg Ile Cys Glu Lys Asn Ala Lys
                180                 185

<210> SEQ ID NO 66
<211> LENGTH: 113
<212> TYPE: PRT
<213> ORGANISM: Homo sapiens

<400> SEQUENCE: 66

Met Gly Gly Leu Glu Pro Cys Ser Arg Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys

<210> SEQ ID NO 67
<211> LENGTH: 116
<212> TYPE: PRT
<213> ORGANISM: Artificial Sequence
<220> FEATURE:
<223> OTHER INFORMATION: Humanized variable heavy chain

<400> SEQUENCE: 67

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Gly Phe Asn Asn Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Ser Gly Asn Thr Tyr Tyr Asn Glu Asn Phe
 50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Gly Lys Glu Ser Phe Ala Tyr Trp Gly Gln Gly Thr Leu Val
                100                 105                 110

Thr Val Ser Ser
        115

<210> SEQ ID NO 68
<211> LENGTH: 121
<212> TYPE: PRT
<213> ORGANISM: Artificial Sequence
<220> FEATURE:
<223> OTHER INFORMATION: Humanized variable heavy chain

<400> SEQUENCE: 68

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ile Tyr
            20                  25                  30

Ala Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
 50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Ser Ser Glu Val Phe Tyr Asp Tyr Arg Phe Asp Tyr Trp Gly
                100                 105                 110

Gln Gly Thr Leu Val Thr Val Ser Ser
        115                 120

<210> SEQ ID NO 69
<211> LENGTH: 114
<212> TYPE: PRT
<213> ORGANISM: Artificial Sequence
<220> FEATURE:
<223> OTHER INFORMATION: Humanized variable light chain

<400> SEQUENCE: 69

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Phe Asn Phe
            20                  25                  30

Ser Asn Arg Asn Asn Tyr Leu Ala Trp Tyr Gln Gln Lys Pro Gly Gln
        35                  40                  45

Pro Pro Lys Leu Leu Ile Tyr Phe Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80
```

```
Ile Ser Ser Leu Gln Ala Glu Asp Val Ala Val Tyr Tyr Cys Gln Gln
                85                  90                  95

His Phe Thr Thr Pro Tyr Thr Phe Gly Gln Gly Thr Lys Val Glu Ile
            100                 105                 110

Lys Arg

<210> SEQ ID NO 70
<211> LENGTH: 108
<212> TYPE: PRT
<213> ORGANISM: Artificial Sequence
<220> FEATURE:
<223> OTHER INFORMATION: Humanized variable light chain

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Ser
            20                  25                  30

Leu Asn Trp Tyr Gln Gln Lys Pro Gly Lys Ala Pro Lys Leu Leu Ile
        35                  40                  45

Tyr Ala Thr Ser Asn Leu Asp Ser Gly Val Pro Ser Arg Phe Ser Gly
50                  55                  60

Ser Gly Ser Gly Thr Asp Phe Thr Leu Thr Ile Ser Leu Gln Pro
65                  70                  75                  80

Glu Asp Phe Ala Thr Tyr Tyr Cys Leu Gln Tyr Ala Ser Ser Pro Phe
                85                  90                  95

Thr Phe Gly Gln Gly Thr Lys Val Glu Ile Lys Arg
            100                 105

<210> SEQ ID NO 71
<211> LENGTH: 95
<212> TYPE: PRT
<213> ORGANISM: Homo sapiens

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 72
<211> LENGTH: 100
<212> TYPE: PRT
<213> ORGANISM: Homo sapiens

<400> SEQUENCE: 72

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

```
Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro
            100

<210> SEQ ID NO 73
<211> LENGTH: 96
<212> TYPE: PRT
<213> ORGANISM: Homo sapiens

<400> SEQUENCE: 73

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

<210> SEQ ID NO 74
<211> LENGTH: 101
<212> TYPE: PRT
<213> ORGANISM: Homo sapiens

<400> SEQUENCE: 74

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                 20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro
            100

<210> SEQ ID NO 75
<211> LENGTH: 98
<212> TYPE: PRT
<213> ORGANISM: Homo sapiens

<400> SEQUENCE: 75

Gln Val Gln Leu Val Gln Ser Gly Ala Glu Val Lys Lys Pro Gly Ala
 1               5                  10                  15
```

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 76
<211> LENGTH: 98
<212> TYPE: PRT
<213> ORGANISM: Homo sapiens

<400> SEQUENCE: 76

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 77
<211> LENGTH: 97
<212> TYPE: PRT
<213> ORGANISM: Homo sapiens

<400> SEQUENCE: 77

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

ANTI-MDL-1 ANTIBODIES

FIELD OF THE INVENTION

The present invention relates generally to antibodies specific for myeloid DAP-12 associating lectin (MDL-1) and uses thereof. More specifically, the invention relates to humanized antibodies that recognize human MDL-1 and modulate its activity, particularly in immune disorders.

The Sequence Listing filed electronically herewith is also hereby incorporated by reference in its entirety (File Name: "BP06640US01_SeqListing.txt"; Date Created Aug. 23, 2011; File Size: 37.8 KB.)

BACKGROUND OF THE INVENTION

Several receptor complexes that play a role in leukocyte activation and inflammatory responses (Gingras et al. (2001) Mol. Immun. 38:817-824) are formed by the non-covalent association of the transmembrane adaptor glycoprotein DAP12 with receptors of the Ig superfamily (Bouchon et al. (2000) J. Immunol. 164:4991-4995; Dietrich et al. (2000) J. Immunol. 164:9-12) or the C-type lectin superfamily (Bakker et al. (1999) PNAS U.S.A. 96:9792-9796). These associations are formed by the interaction of a negatively charged amino acid residue (aspartic acid) located in the DAP12 transmembrane domain with a positively charged amino acid residue (lysine) located in the transmembrane domain of these receptors (Gingras et al. (2001) Mol. Immun. 38:817-824).

DAP12 is a disulfide-bonded, homodimeric type I transmembrane glycoprotein containing an immunoreceptor tyrosine-based activation motif (ITAM) located in its intracellular domain (Lanier, et al. (1998) Nature 391:703-707; WO 99/06557; Campbell and Colonna (1999) Int. J. Biochem. Cell Biol. 31:631-636; Lanier and Bakker (2000) Immunol. Today 21:611-614). The importance of DAP12 relies on the ITAM domain (Gingras et al. (2001) Mol. Immun. 38:817-824). Because the intracellular domain of the receptors of the Ig superfamily (Bouchon et al. (2000) J. Immunol. 164:4991-4995; Dietrich et al. (2000) J. Immunol. 164:9-12) and the C-type lectin superfamily (Bakker et al. (1999) PNAS U.S.A. 96:9792-9796) that non-covalently associate with DAP12 are too short to allow interaction with other molecules, the DAP12 cytoplasmic domain constitutes the signaling subunit of these receptor complexes. Upon engagement of the receptor ligand-binding subunit, the DAP12 cytoplasmic ITAM is phosphorylated by Src kinases. The ITAM of DAP12 then interacts with Syk cytoplasmic tyrosine kinases, which initiates a cascade of events that leads to activation (Lanier et al. (1998) Nature 391:703-707; Campbell and Colonna (1999) Int. J. Biochem. Cell Biol. 31:631-636; Lanier and Bakker (2000) Immunol. Today 21:611-614).

DAP12 is expressed in monocytes, macrophages, natural killer (NK) cells, granulocytes, dendritic cells and mast cells, where it provides signaling function for at least eight distinct receptors (Gingras et al. (2001) Mol. Immun. 38:817-824; Lanier and Bakker, (2000) Immunol. Today 21:611-614). The myeloid receptor of the C-type lectin superfamily associated with DAP12 is Myeloid DAP12-associating Lectin-1 (MDL-1), a type II transmembrane protein. MDL-1 was the first DAP12 associating molecule to be identified and cloned (Bakker et al. (1999) PNAS USA 96(17):9792-9796). It is expressed exclusively in monocytes and macrophages (Bakker et al. (1999) supra) as well as on other myeloid cell types such as, neutrophils and dendritic cells. The presence of a negatively charged residue in the transmembrane domain of DAP12 precludes its cell surface expression in the absence of a partner receptor, such as MDL-1, which has a positively charged residue in its transmembrane domain. However, DAP12 alone is not sufficient for its expression and function at the cell surface. Thus, the combination of a DAP12-associating molecule, such as MDL-1, and DAP12 may account for transmitting a particular physiological signal via DAP12 (Nochi et al. (2003) Am. J. of Pathology 162:1191-1201).

The need exists for improved methods and compositions for the treatment of immune mediated disorders, in particular, infectious diseases, by use of agents that modulate DAP12 signaling through the use of agonists against MDL-1. Preferably, such agonists would have a high affinity for the target molecule, and would be able to stimulate the MDL-1 mediated DAP-12 signaling at relatively low doses. Preferably, such methods and compositions would be highly specific for MDL-1, and not interfere with the activity of other activating or inhibitory receptors, such as TREM-1. Preferably, such methods and compositions would employ agonists suitable for modification for or the delivery of cytotoxic payloads to target cells, but also suitable for non-cytotoxic uses. Preferably, such methods and compositions would employ antibodies modified to limit their antigenicity when administered to a subject in need thereof.

SUMMARY OF THE INVENTION

The present invention meets these needs in the art and more by providing agonists of MDL-1, e.g. humanized anti-MDL-1 antibodies.

In one aspect the invention provides binding compounds, such as an antibodies or fragment thereof, including humanized or chimeric recombinant antibodies, that binds human MDL-1, comprising an antibody light chain variable domain, or antigen binding fragment thereof, having at least one or more CDRs selected from the group consisting of SEQ ID NOs: 41-64 and at least one or more CDRs selected from the group consisting of SEQ ID NOs: 17-40.

In other embodiments the binding compound of the present invention comprises a light chain variable domain and a heavy chain variable domain, or the antigen binding fragments thereof, described in the preceding two paragraphs.

In some embodiments, the binding compound comprises a framework region, wherein the amino acid sequence of the framework region is all or substantially all of a human immunoglobulin amino acid sequence.

In some embodiments the light chain variable domain comprises a sequence selected from the group consisting of SEQ ID NOs: 9-16 or a variant thereof. In some embodiments the heavy chain variable domain comprises a sequence selected from the group consisting of SEQ ID NOs: 1-8. In yet a further embodiment, the binding compound comprises a light chain variable domain and a heavy chain variable domain, or the antigen binding fragments thereof, described in this paragraph.

In other embodiments the binding compound of the present invention comprises a light chain variable domain, or an antigen binding fragment thereof, consisting essentially of a sequence selected from the group consisting of SEQ ID NOs: 9-16, and/or a heavy chain variable domain, or an antigen binding fragment thereof, consisting essentially of a sequence selected from the group consisting of SEQ ID NOs: 1-8.

In one embodiment, the invention relates to antibodies that are able to block the binding of a binding compound of the present invention to human MDL-1 in a cross-blocking assay. In various embodiments the antibody is able to block binding of human MDL-1 to an antibody comprising the CDR sequences of antibodies DX230, DX241, DX244, DX246, DX297, DX233, DX239, and DX240 as disclosed herein. In other embodiments, the antibody is able to block binding of human MDL-1, in a cross-blocking assay, to the antibodies (clones DX230, DX241, DX244, DX246, DX297, DX233, DX239, DX240) deposited with ATCC under accession numbers PTA-8373, PTA-8374, PTA-8375, PTA-8376, and PTA-8377, on Apr. 23, 2007, or deposited with ATCC under accession numbers, PTA-9134, PTA-9135, and PTA-9136, on Apr. 8, 2008. In another embodiment, the invention relates to binding compounds that are able to block MDL-1-mediated activity, such activities including but not limited to, mediating the degranulation of mast cells in an appropriate mast cell assay.

In some embodiments, the binding compound of the present invention comprises a humanized antibody comprising the CDRs, or variants thereof, selected from the CDRs of the antibodies disclosed herein, in combination with human germline light chain and heavy chain variable domain framework sequences in place of the rodent frameworks of the parental antibodies.

In some embodiments, the binding compound of the present invention further comprises a heavy chain constant region, wherein the heavy chain constant region comprises a γ1, γ2, γ3, or γ4 human heavy chain constant region or a variant thereof. In various embodiments the light chain constant region comprises a lambda or a kappa human light chain constant region.

In various embodiments the binding compounds of the present invention are polyclonal, monoclonal, chimeric, humanized or fully human antibodies or fragments thereof. The present invention also contemplates that the antigen binding fragment is an antibody fragment selected from the group consisting of Fab, Fab', Fab'-SH, Fv, scFv, F(ab')$_2$, and a diabody.

The present invention encompasses a method of enhancing an immune response in a human subject comprising administering to a subject in need thereof an antibody (or a antigen binding fragment thereof) specific for MDL-1 in an amount effective to stimulate MDL-1 signaling. In some embodiments, the antibody specific for MDL-1 is the humanized or chimeric antibody. In further embodiments, the immune response is an anti-infective response.

The present invention encompasses an isolated nucleic acid encoding the polypeptide sequence of an antibody embodiment of the binding compound of the present invention. The nucleic acid can be in an expression vector operably linked to control sequences recognized by a host cell transfected with the vector. Also encompassed is a host cell comprising the vector, and a method of producing a polypeptide comprising culturing the host cell under conditions wherein the nucleic acid sequence is expressed, thereby producing the polypeptide, and recovering the polypeptide from the host cell or medium.

In various embodiments, the invention relates to use of a binding compound of the present invention in the manufacture of medicaments for the treatment of immune disorders including, infectious diseases (e.g. bacterial, mycobacterial, viral or fungal infection, including chronic infections and sepsis.

In other embodiments the invention relates to pharmaceutical compositions comprising a binding compound of the present invention for treating immune disorders including, infectious diseases (e.g. bacterial, mycobacterial, viral or fungal infection, including chronic infections), and sepsis.

In another embodiment, the present invention encompasses a humanized MDL-1 antibody comprising an antibody heavy chain variable domain of SEQ ID NO: 67 or SEQ ID NO: 68 and an antibody light chain variable domain of SEQ ID NO: 69 or SEQ ID NO: 70.

BRIEF DESCRIPTION OF THE DRAWINGS

FIG. 1 shows a comparison of DX230, DX241, DX244, DX246, and DX297 anti-MDL-1 antibodies variable heavy chain sequences.

FIG. 2 shows a comparison of DX233, DX239, and DX240 anti-MDL-1 antibodies variable heavy chain sequences.

FIG. 3 shows a comparison of DX230, DX241, DX244, DX246, and DX297 anti-MDL-1 antibodies variable light chain sequences.

FIG. 4 shows a comparison of DX233, DX239, and DX240 anti-MDL-1 antibodies variable heavy chain sequences.

FIG. 5 shows humanization calculations for the variable regions of the light (FIG. 5A) and heavy (FIG. 5B) chains of the DX239 anti-human MDL-1 antibody and for the variable regions of the light (FIG. 5C) and heavy (FIG. 5D) chains of the DX244 anti-human MDL-1 antibody.

DETAILED DESCRIPTION

Figure 6:
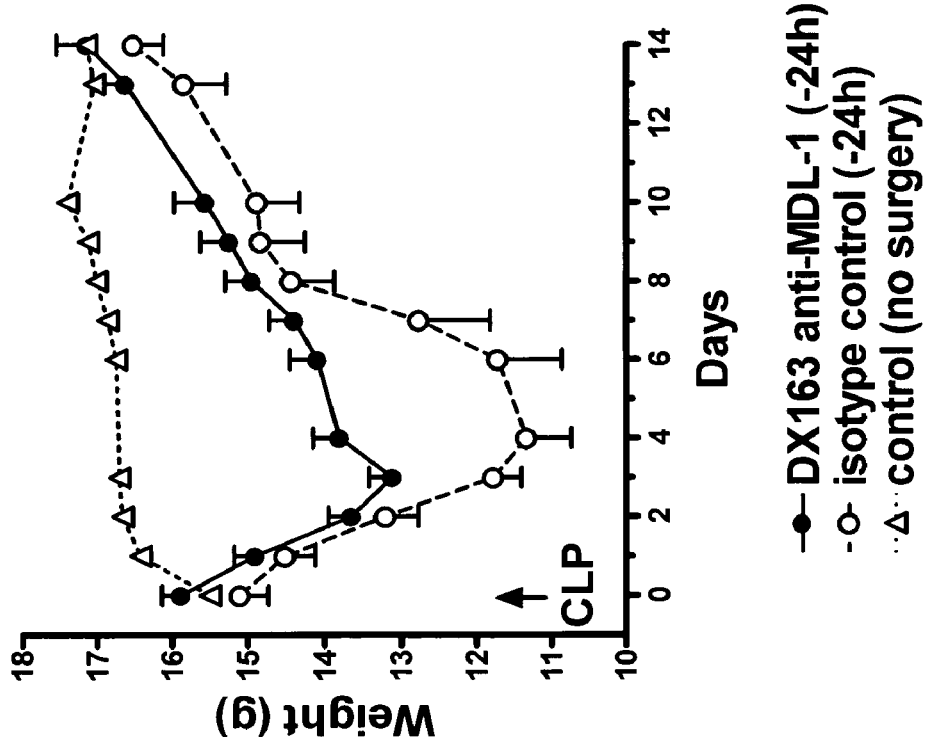
FIG. 6 shows weight measurements of post CLP mice.

As used herein, including the appended claims, the singular forms of words such as "a," "an," and "the," include their corresponding plural references unless the context clearly dictates otherwise. Table 15 below provides a listing of sequence identifiers used in this application. All references cited herein are incorporated by reference to the same extent as if each individual publication, database entry (e.g. Genbank sequences or GeneID entries), patent application, or patent, was specifically and individually indicated to be incorporated by reference. Citation of the references herein is not intended as an admission that any of the foregoing is pertinent prior art, nor does it constitute any admission as to the contents or date of these publications or documents.

I. Definitions

The terms "MDL-1", "Myeloid DAP12 associating lectin-1", "Myeloid DAP12-associated lectin-1", "DAP-12", "DAP12", "DNAX Activation Protein, 12 kD" are well known in the art. The human and mouse DAP12 and MDL-1 nucleotide and polypeptide sequences are disclosed in WO 99/06557. GenBank® deposits of the human MDL-1 nucleic acid sequence (AR217548) and mouse MDL-1 nucleic and amino acid sequences (AR217549 and AAN21593, respectively) are also available.

"Proliferative activity" encompasses an activity that promotes, that is necessary for, or that is specifically associated with, e.g., normal cell division, as well as cancer, tumors, dysplasia, cell transformation, metastasis, and angiogenesis.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an agent with animal subject, a cell, tissue, physiological compartment, or physiological fluid. "Treatment of a cell" also encompasses situations where the agent contacts MDL-1 (MDL-1/DAP12 heterodimer), e.g., in the fluid phase or colloidal phase, but also situations where the agonist or antagonist does not contact the cell or the receptor.

As used herein, the term "antibody" refers to any form of antibody that exhibits the desired biological activity. Thus, it is used in the broadest sense and specifically covers monoclonal antibodies (including full length monoclonal antibodies), polyclonal antibodies, multispecific antibodies (e.g., bispecific antibodies), chimeric antibodies, humanized antibodies, fully human antibodies, etc. so long as they exhibit the desired biological activity.

As used herein, the terms "MDL-1 binding fragment," "binding fragment thereof" or "antigen binding fragment thereof" encompass a fragment or a derivative of an antibody that still substantially retains its biological activity of inhibiting DAP12 signaling mediated by MDL-1, such inhibition being referred to herein as "MDL-1 inhibitory activity." Because antagonists of MDL-1 will have the biological activity of inhibiting DAP12 signaling, such antagonists are said (interchangeably) to inhibit DAP12, inhibit MDL-1, or inhibit both MDL-1/DAP12. The term "antibody fragment" or MDL-1 binding fragment refers to a portion of a full length antibody, generally the antigen binding or variable region thereof. Examples of antibody fragments include Fab, Fab', F(ab')$_2$, and Fv fragments; diabodies; linear antibodies; single-chain antibody molecules, e.g., sc-Fv; and multispecific antibodies formed from antibody fragments. Typically, a binding fragment or derivative retains at least 10% of its MDL-1 inhibitory activity. Preferably, a binding fragment or derivative retains at least 25%, 50%, 60%, 70%, 80%, 90%, 95%, 99% or 100% (or more) of its MDL-1 inhibitory activity, although any binding fragment with sufficient affinity to exert the desired biological effect will be useful. It is also intended that a MDL-1 binding fragment can include variants having conservative amino acid substitutions that do not substantially alter its biologic activity.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. U.S. Pat. No. 4,816,567; Morrison et al. (1984) *Proc. Natl. Acad. Sci. USA* 81: 6851-6855.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun (1994) THE PHARMACOLOGY OF MONOCLONAL ANTIBODIES, vol. 113, Rosenburg and Moore eds. Springer-Verlag, New York, pp. 269-315.

The monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

The antibodies of the present invention also include antibodies with modified (or blocked) Fc regions to provide altered effector functions. See, e.g., U.S. Pat. No. 5,624,821; WO2003/086310; WO2005/120571; WO2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta (2005) *J. Allergy Clin. Immunol.* 116:731 at 734-35.

The antibodies of the present invention also include antibodies with intact Fc regions that provide full effector functions, e.g. antibodies of isotype IgG1, which induce complement-dependent cytotoxicity (CDC) or antibody dependent cellular cytotoxicity (ADCC) in the a targeted cell.

The antibodies of the present invention also include antibodies conjugated to cytotoxic payloads, such as cytotoxic agents or radionuclides. Such antibody conjugates may be used in immunotherapy to selectively target and kill cells expressing MDL-1 and/or DAP12 on their surface. Exemplary cytotoxic agents include ricin, vinca alkaloid, methotrexate, *Psuedomonas* exotoxin, saporin, diphtheria toxin, cisplatin, doxorubicin, abrin toxin, gelonin and pokeweed antiviral protein. Exemplary radionuclides for use in immunotherapy with the antibodies of the present invention include $^{125}$I, $^{131}$I, $^{90}$Y, $^{67}$Cu, $^{211}$At, $^{177}$Lu, $^{143}$Pr and $^{213}$Bi. See, e.g., U.S. Patent Application Publication No. 2006/0014225.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively. A fully human antibody may be generated in a human being, in a transgenic animal having human immunoglobulin germline sequences, by phage display or other molecular biological methods.

As used herein, the term "hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain (Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain (Chothia and Lesk (1987) *J. Mol. Biol.* 196: 901-917). As used herein, the term "framework" or "FR" residues refers to those variable domain residues other than the hypervariable region residues defined herein as CDR residues. The residue numbering above relates to the Kabat numbering system and does not necessarily correspond in detail to the sequence numbering in the accompanying Sequence Listing.

"Binding compound" refers to a molecule, small molecule, macromolecule, polypeptide, antibody or fragment or analogue thereof, or soluble receptor, capable of binding to a target. "Binding compound" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, that is capable of binding to a target. When used with reference to antibodies, the term "binding compound" refers to both antibodies and antigen binding fragments thereof. "Binding" refers to an association of the binding composition with a target where the association results in reduction in the normal Brownian motion of the binding composition, in cases where the binding composition can be dissolved or suspended in solution. "Binding composition" refers to a molecule, e.g. a binding compound, in combination with a stabilizer, excipient, salt, buffer, solvent, or additive, capable of binding to a target.

"Conservatively modified variants" or "conservative substitution" refers to substitutions of amino acids are known to those of skill in this art and may often be made even in essential regions of the polypeptide without altering the biological activity of the resulting molecule. Such exemplary substitutions are preferably made in accordance with those set forth in Table 1 as follows:

TABLE 1

Exemplary Conservative Amino Acid Substitutions

| Original residue | Conservative substitution |
| --- | --- |
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Those of skill in this art recognize that, in general, single amino acid substitutions in non-essential regions of a polypeptide may not substantially alter biological activity. See, e.g., Watson et al. (1987) *Molecular Biology of the Gene*, The Benjamin/Cummings Pub. Co., p. 224 (4th Edition).

The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a binding compound that consists essentially of a recited amino acid sequence may also include one or more amino acids, including substitutions of one or more amino acid residues, that do not materially affect the properties of the binding compound.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side affects. See, e.g., U.S. Pat. No. 5,888,530. An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject. See, e.g., Maynard et al. (1996) *A Handbook of SOPs for Good Clinical Practice*, Interpharm Press, Boca Raton, Fla.; Dent (2001) *Good Laboratory and Good Clinical Practice*, Urch Publ., London, UK.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

"Infection" as used herein is an invasion and multiplication of microorganisms in tissues of a subject's body. The infection or "infectious disease" may be clinically inapparent or result in local cellular injury due to competitive metabolism, toxins, intracellular replication, or antigen-antibody response. The infection may remain localized, subclinical and temporary if the body's defensive mechanisms are effective. A local invention may persist and spread by extension to become an acute, subacute, or chronic clinical infection or disease state. A local infection may also become systemic when the microorganisms gain access to the lymphatic or vascular system. Infectious diseases include bacterial, viral, parasitic, opportunistic, or fungal infections.

As used herein, the term "cancer" refers to a group of cells (usually derived from a single cell) that has lost its normal control mechanisms and thus has unregulated growth. Cancerous tissues or malignancies include those of the blood and blood-forming tissues, such as leukemias and lymphomas, and solid tumors, often termed cancer. Such cancers may be carcinomas or sarcomas.

As used herein, the term "tumor" refers to an abnormal growth or mass. Tumors may be benign or cancerous (malignant). Benign tumors are not cancer. Benign tumors may be removed from the body, and then seldom grow back. Cells from a benign tumor do not spread to surrounding tissues or to other parts of the body.

As cancerous cells grow and multiply, they form a mass of cancerous tissue, that is a tumor, which invades and destroys normal adjacent tissues. Malignant tumors are cancer. Malignant tumors usually can be removed, but they may grow back. Cells from malignant tumors can invade and damage nearby tissues and organs. Also, cancer cells can break away from a malignant tumor and enter the bloodstream or lymphatic system, which is the way cancer cells spread from the primary tumor (i.e., the original cancer) to form new tumors in other organs. The spread of cancer in the body is called metastasis (What You Need to Know About Cancer—an Overview, NIH Publication No. 00-1566; posted Sep. 26, 2000, updated Sep. 16, 2002 (2002)).

As used herein, the term "solid tumor" refers to an abnormal growth or mass of tissue that usually does not contain cysts or liquid areas. Solid tumors may be benign (not cancerous) or malignant (cancerous). Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

As used herein, the term "primary cancer" refers to the original tumor or the first tumor. Cancer may begin in any organ or tissue of the body. It is usually named for the part of the body or the type of cell in which it originates (Metastatic Cancer: Questions and Answers, Cancer Facts 6.20, National Cancer Institute, reviewed Sep. 1, 2004 (2004)).

As used herein, the term "carcinoma in situ" refers to cancerous cells that are still contained within the tissue where they started to grow, and have not yet become invasive or spread to other parts of the body.

As used herein, the term "carcinomas" refers to cancers of epithelial cells, which are cells that cover the surface of the body, produce hormones, and make up glands. Examples of carcinomas are cancers of the skin, lung, colon, stomach, breast, prostate and thyroid gland.

As used herein, the term "sepsis" refers to a morbid condition induced by a toxin, the introduction or accumulation of which is most commonly caused by a microbial infection or trauma. The initial symptoms of sepsis typically include chills, profuse sweat, irregularly remittent fever, prostration and the like, followed by persistent fever, hypotension leading to shock, neutropenia, leukopenia, disseminated intravascular coagulation, adult respiratory distress syndrome and multiple organ failure.

As used herein "antibiotic" refers to an aminoglycoside such as gentamycin or a beta-lactam such as penicillin, cephalosporin and the like. Also included are known anti-fungals and anti-virals. Antiboitics can be used with the MDL-1 antibodies of the present invention to provide additional efficacy to clear the infection and/or prevent the development of sepsis.

As used herein, the term "isolated nucleic acid molecule" refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences involved in the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence.

For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific piece of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, the term "germline sequence" refers to a sequence of unrearranged immunoglobulin DNA sequences, including rodent (e.g. mouse) and human germline sequences. Any suitable source of unrearranged immunoglobulin DNA may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. (2005) *Nucleic Acids Res.* 33:D256-D261.

To examine the extent of enhancement of MDL-1/DAP12 activity, for example, samples or assays comprising a given, e.g., protein, gene, cell, or organism, are treated with a potential activating or inhibiting agent and are compared to control samples without the agent. Control samples, i.e., not treated with agent, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) *Glia* 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

"Small molecule" is defined as a molecule with a molecular weight that is less than 10 kDa, typically less than 2 kDa, and preferably less than 1 kDa. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described. See, e.g., Casset et al. (2003) *Biochem. Biophys. Res. Commun.* 307:198-205; Muyldermans (2001) *J. Biotechnol.* 74:277-302; Li (2000) *Nat. Biotechnol.* 18:1251-1256; Apostolopoulos et al. (2002) *Curr. Med. Chem.* 9:411-420; Monfardini et al. (2002) *Curr. Pharm. Des.* 8:2185-2199; Domingues et al. (1999) *Nat. Struct. Biol.* 6:652-656; Sato and Sone (2003) *Biochem. J.* 371:603-608; U.S. Pat. No. 6,326,482.

"Specifically" or "selectively" binds, when referring to a ligand/receptor, antibody/antigen, or other binding pair, indicates a binding reaction that is determinative of the presence of the protein in a heterogeneous population of proteins and other biologics. Thus, under designated conditions, a specified ligand binds to a particular receptor and does not bind in a significant amount to other proteins present in the sample. As used herein, an antibody is said to bind specifically to a polypeptide comprising a given sequence (in this case MDL-1) if it binds to polypeptides comprising the sequence of MDL-1 but does not bind to proteins lacking the sequence of MDL-1. For example, an antibody that specifically binds to a polypeptide comprising MDL-1 may bind to a FLAG®-tagged form of MDL-1 but will not bind to other FLAG®-tagged proteins.

The antibody, or binding composition derived from the antigen-binding site of an antibody, of the contemplated method binds to its antigen with an affinity that is at least two fold greater, preferably at least ten times greater, more preferably at least 20-times greater, and most preferably at least 100-times greater than the affinity with unrelated antigens. In a preferred embodiment the antibody will have an affinity that is greater than about $10^9$ liters/mol, as determined, e.g., by Scatchard analysis. Munsen et al. (1980) *Analyt. Biochem.* 107:220-239.

II. General

The present invention provides engineered anti-MDL-1 antibodies and uses thereof to treat immune disorders, in particular impaired response to infectious diseases and cancer.

Previous studies have found that MDL-1 and other DAP12 associated molecules, are differentially expressed during host responses to mycobacterial infections (see, e.g., Aoki, et al. (2004) *Infection and Immunity* 72:2477-2483). In particular, MDL-1 expression was upregulated in macrophages during a mycobacterial infection. IFNγ treatment of these macrophages also increased MDL-1 expression.

US 2006/0099144 and WO 2006/052975 both describe increased expression of MDL-1 by macrophages in various cancer cells (e.g., melanoma, ovarian, breast, colorectal, renal and stomach cancers). Thus the antibodies of the present invention should be useful in stimulating the immune system in response to infections and cancer. Additionally the antibodies of the present invention can also be used to clear these microbial infections, thereby preventing the development of sepsis.

III. Generation of MDL-1 Specific Antibodies

Any suitable method for generating monoclonal antibodies may be used. For example, a recipient may be immunized with MDL-1 or a fragment thereof. Any suitable method of immunization can be used. Such methods can include adjuvants, other immunostimulants, repeated booster immunizations, and the use of one or more immunization routes. Any suitable source of MDL-1 can be used as the immunogen for the generation of the non-human antibody of the compositions and methods disclosed herein. Such forms include, but are not limited whole protein, peptide(s), and epitopes generated through recombinant, synthetic, chemical or enzymatic degradation means known in the art. In preferred embodiments the immunogen comprises the extracellular portion of MDL-1. The domain structure of MDL-1 is discussed in Bakker, et al. supra.; WO 99/06557; and GenBank Accession number AAF02491. A short intracellular region encompasses residues 1 and 2, of SEQ ID NO: 65. The transmembrane region is identified as running from about residue 6 through residue 27, of SEQ ID NO: 65. A C-type lectin-like domain of the type found in natural killer cell receptors (NKRs) is found from about residue 71 to residue 184, of SEQ ID NO: 65.

Any form of the antigen can be used to generate the antibody that is sufficient to generate a biologically active antibody. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids.

Any suitable method can be used to elicit an antibody with the desired biologic properties to enhance MDL-1/DAP12 signaling. It is desirable to prepare monoclonal antibodies (mAbs) from various mammalian hosts, such as mice, rats, other rodents, humans, other primates, etc. Description of techniques for preparing such monoclonal antibodies may be found in, e.g., Stites et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Thus, monoclonal antibodies may be obtained by a variety of techniques familiar to researchers skilled in the art. Typically, spleen cells from an animal immunized with a desired antigen are immortalized, commonly by fusion with a myeloma cell. See Kohler and Milstein (1976) *Eur. J. Immunol.* 6:511-519. Alternative methods of immortalization include transformation with Epstein Barr Virus, oncogenes, or retroviruses, or other methods known in the art. See, e.g., Doyle et al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences that encode a monoclonal antibody or a antigen binding fragment thereof by screening a DNA library from human B cells according, e.g., to the general protocol outlined by Huse et al. (1989) *Science* 246:1275-1281.

Other suitable techniques involve selection of libraries of antibodies in phage or similar vectors. See, e.g., Huse et al. supra; and Ward et al. (1989) *Nature* 341:544-546. The polypeptides and antibodies of the present invention may be used with or without modification, including chimeric or humanized antibodies. Frequently, the polypeptides and antibodies will be labeled by joining, either covalently or non-covalently, a substance that provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly U.S. Pat. No. 4,816,567; and Queen et al. (1989) *Proc. Nat'l Acad. Sci. USA* 86:10029-

10033; or made in transgenic mice, see Mendez et al. (1997) *Nature Genetics* 15:146-156. See also Abgenix and Medarex technologies.

Antibodies or binding compositions against predetermined fragments of MDL-1 can be raised by immunization of animals with conjugates of the polypeptide, fragments, peptides, or epitopes with carrier proteins. Monoclonal antibodies are prepared from cells secreting the desired antibody. These antibodies can be screened for binding to normal or defective MDL-1. These monoclonal antibodies will usually bind with at least a $K_d$ of about 1 µM, more usually at least about 300 nM, 30 nM, 10 nM, 3 nM, 1 nM, 300 pM, 100 pM, 30 pM or better, usually determined by ELISA. Suitable non-human antibodies may also be identified using the biologic assays described in Examples 5 and 6, below.

Hybridomas expressing antibody clones DX230, DX241, DX244, DX246, and DX297 were deposited pursuant to the Budapest Treaty with American Type Culture Collection (ATCC—Manassas, Va., USA) on Apr. 23, 2007 under Accession Numbers PTA-8373, PTA-8374, PTA-8375, PTA-8376, and PTA-8377, respectively. Hybridomas expressing antibody clones DX230, DX239 and DX240 were deposited pursuant to the Budapest Treaty with American Type Culture Collection (ATCC—Manassas, Va., USA) on Apr. 8, 2008 under Accession Numbers PTA PTA-9134, PTA-9135, and PTA-9136, respectively.

IV. Humanization of MDL-1 Specific Antibodies

Any suitable non-human antibody can be used as a source for the hypervariable region. Sources for non-human antibodies include, but are not limited to, murine (e.g. *Mus musculus*), rat (e.g. *Rattus norvegicus*), Lagomorphs (including rabbits), bovine, and primates. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance of the desired biological activity. For further details, see Jones et al. (1986) *Nature* 321:522-525; Reichmann et al. (1988) *Nature* 332:323-329; and Presta (1992) *Curr. Op. Struct. Biol.* 2:593-596.

Methods for recombinantly engineering antibodies have been described, e.g., by Boss et al. (U.S. Pat. No. 4,816,397), Cabilly et al. (U.S. Pat. No. 4,816,567), Law et al. (European Patent Application Publication No. 438310) and Winter (European Patent Application Publication No. 239400).

Amino acid sequence variants of humanized anti-MDL-1 antibody are prepared by introducing appropriate nucleotide changes into the humanized anti-MDL-1 antibody DNA, or by peptide synthesis. Such variants include, for example, deletions from, and/or insertions into, and/or substitutions of, residues within the amino acid sequences shown for the humanized anti-MDL-1 antibody. Any combination of deletion, insertion, and substitution is made to arrive at the final construct, provided that the final construct possesses the desired characteristics. The amino acid changes also may alter post-translational processes of the humanized anti-MDL-1 antibody, such as changing the number or position of glycosylation sites.

A useful method for identification of certain residues or regions of the humanized anti-MDL-1 antibody polypeptide that are preferred locations for mutagenesis is called "alanine scanning mutagenesis," as described by Cunningham and Wells (1989) *Science* 244: 1081-1085. Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with MDL-1 antigen. The amino acid residues demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed humanized anti-MDL-1 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include humanized anti-MDL-1 antibody with an N-terminal methionyl residue or the antibody fused to an epitope tag. Other insertional variants of the humanized anti-MDL-1 antibody molecule include the fusion to the N- or C-terminus of humanized anti-MDL-1 antibody of an enzyme or a polypeptide that increases the serum half-life of the antibody.

Another type of variant is an amino acid substitution variant. These variants have at least one amino acid residue in the humanized anti-MDL-1 antibody molecule removed and a different residue inserted in its place. The sites of greatest interest for substitutional mutagenesis include the hypervariable loops, but FR alterations are also contemplated.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Yet another type of amino acid variant is the substitution of residues to provide for greater chemical stability of the final humanized antibody. For example, an asparagine (N) residue may be changed to reduce the potential for formation of isoaspartate at any NG sequences within a rodent CDR. A similar problem may occur at a DG sequence. Reissner and Aswad (2003) *Cell. Mol. Life Sci.* 60:1281. Isoaspartate formation may debilitate or completely abrogate binding of an antibody to its target antigen. Presta (2005) *J. Allergy Clin. Immunol.* 116:731 at 734. In one embodiment, the asparagine is changed to glutamine (Q). In addition, methionine residues in rodent CDRs may be changed to reduce the possibility that the methionine sulfur would oxidize, which could reduce antigen binding affinity and also contribute to molecular heterogeneity in the final antibody preparation. Id. In one embodiment, the methionine is changed to alanine (A). Antibodies with such substitutions are subsequently screened to ensure that the substitutions do not decrease MDL-1 binding affinity to unacceptable levels.

Nucleic acid molecules encoding amino acid sequence variants of humanized MDL-1 specific antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-MDL-1 antibody.

Ordinarily, amino acid sequence variants of the humanized anti-MDL-1 antibody will have an amino acid sequence having at least 75% amino acid sequence identity with the original humanized antibody amino acid sequences of either the heavy or the light chain more preferably at least 80%, more preferably at least 85%, more preferably at least 90%, and most preferably at least 95%, 98% or 99%. Identity or homology with respect to this sequence is defined herein as the percentage of amino acid residues in the candidate sequence that are identical with the humanized anti-MDL-1 residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

The humanized antibody can be selected from any class of immunoglobulins, including IgM, IgG, IgD, IgA, and IgE. Preferably, the antibody is an IgG antibody. Any isotype of IgG can be used, including $IgG_1$, $IgG_2$, $IgG_3$, and $IgG_4$. Variants of the IgG isotypes are also contemplated. The humanized antibody may comprise sequences from more than one class or isotype. Optimization of the necessary constant domain sequences to generate the desired biologic activity is readily achieved by screening the antibodies in the biological assays described in the Examples.

Likewise, either class of light chain can be used in the compositions and methods herein. Specifically, kappa, lambda, or variants thereof are useful in the present compositions and methods.

Any suitable portion of the CDR sequences from the non-human antibody can be used. The CDR sequences can be mutagenized by substitution, insertion or deletion of at least one residue such that the CDR sequence is distinct from the human and non-human antibody sequence employed. It is contemplated that such mutations would be minimal. Typically, at least 75% of the humanized antibody residues will correspond to those of the non-human CDR residues, more often 90%, and most preferably greater than 95%.

Any suitable portion of the FR sequences from the human antibody can be used. The FR sequences can be mutagenized by substitution, insertion or deletion of at least one residue such that the FR sequence is distinct from the human and non-human antibody sequence employed. It is contemplated that such mutations would be minimal. Typically, at least 75% of the humanized antibody residues will correspond to those of the human FR residues, more often 90%, and most preferably greater than 95%, 98% or 99%.

CDR and FR residues are determined according to the standard sequence definition of Kabat. Kabat et al. (1987) Sequences of Proteins of Immunological Interest, National Institutes of Health, Bethesda Md. SEQ ID NOs: 1-8 show the heavy chain variable domain sequences of various rodent anti-human MDL-1 antibodies, and SEQ ID NOs: 9-16 depict the light chain variable domain sequences. FIGS. 1 through 4 provide sequence lineups of heavy and light chain variable domains of the various antibodies of the present invention. CDRs are indicated in the figures, and the individual CDR sequences are each presented with unique Sequence Identifiers (SEQ ID NOs: 17-64), as indicated in Table 18.

TABLE 2

Light Chain Sequences and Domains

| ANTIBODY CLONE | SEQ ID NO: | $V_L$ RESIDUES | LIGHT CHAIN CDR RESIDUES | | |
|---|---|---|---|---|---|
| | | | CDR-L1 | CDR-L2 | CDR-L3 |
| DX230 | 9 | 1-112 | 24-38 | 54-60 | 93-101 |
| DX241 | 10 | 1-108 | 24-34 | 50-56 | 89-97 |
| DX244 | 11 | 1-108 | 24-34 | 50-56 | 89-97 |
| DX246 | 12 | 1-107 | 24-33 | 49-55 | 88-96 |
| DX297 | 13 | 1-112 | 24-38 | 54-60 | 93-101 |
| DX233 | 14 | 1-109 | 24-34 | 50-56 | 89-97 |
| DX239 | 15 | 1-115 | 24-40 | 56-62 | 95-103 |
| DX240 | 16 | 1-114 | 24-40 | 56-62 | 95-102 |

TABLE 3

Heavy Chain Sequences and Domains

| ANTIBODY CLONE | SEQ ID NO: | $V_H$ RESIDUES | HEAVY CHAIN CDR RESIDUES | | |
|---|---|---|---|---|---|
| | | | CDR-H1 | CDR-H2 | CDR-H3 |
| DX230 | 1 | 1-118 | 26-35 | 50-66 | 99-107 |
| DX241 | 2 | 1-119 | 26-35 | 50-66 | 99-108 |
| DX244 | 3 | 1-121 | 26-35 | 50-66 | 99-110 |
| DX246 | 4 | 1-125 | 26-37 | 52-67 | 100-114 |
| DX297 | 5 | 1-118 | 26-35 | 50-66 | 99-107 |
| DX233 | 6 | 1-119 | 26-35 | 50-66 | 99-108 |
| DX239 | 7 | 1-116 | 26-35 | 50-66 | 99-105 |
| DX240 | 8 | 1-118 | 26-35 | 50-66 | 99-107 |

In one embodiment, CDRs include variants of any single sequence CDR disclosed herein (SEQ ID NOs: 17-64), in which the variant comprises 1, 2, 3, 4, 5, 6, 7, 8, 9, 10 or more conservative amino acid substitutions relative to the disclosed sequence, as determined using the data of Table 1.

Also contemplated are chimeric antibodies. As noted above, typical chimeric antibodies comprise a portion of the heavy and/or light chain identical with, or homologous to, corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. See U.S. Pat. No. 4,816,567; and Morrison et al. (1984) *Proc. Natl. Acad. Sci. USA* 81: 6851-6855.

Bispecific antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al. (1983) *Nature* 305: 537-39. Alternatively, bispecific antibodies can be prepared using chemical linkage. See, e.g., Brennan et al. (1985) *Science* 229:81. Bispecific antibodies include bispecific antibody fragments. See, e.g., Holliger et al. (1993) *Proc. Natl. Acad. Sci. U.S.A.* 90:6444-48, Gruber et al. (1994) *J. Immunol.* 152:5368.

In yet other embodiments, different constant domains may be appended to humanized $V_L$ and $V_H$ regions derived from the CDRs provided herein. For example, if a particular intended use of an antibody (or fragment) of the present invention were to call for altered effector functions, a heavy chain constant domain other than IgG1 may be used. Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used.

The parental and engineered forms of the antibodies of the present invention may also be conjugated to a chemical moiety. The chemical moiety may be, inter alia, a polymer, a radionuclide or a cytotoxic factor. Preferably the chemical moiety is a polymer which increases the half-life of the antibody molecule in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee et al., (1999) (Bioconj. Chem. 10:973-981) discloses PEG conjugated single-chain antibodies. Wen et al., (2001) (Bioconj. Chem. 12:545-553) disclose conjugating antibodies with PEG which is attached to a radiometal chelator (diethylenetriaminepentaacetic acid (DTPA)).

The antibodies and antibody fragments or the MDL-1 soluble proteins or fragments thereof of the invention may also be conjugated with labels such as $^{99}Tc$, $^{90}Y$, $^{111}In$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}Ra$, $^{60}Co$, $^{59}Fe$, $^{57}Se$, $^{152}Eu$, $^{67}CU$, $^{217}Ci$, $^{211}At$, $^{212}Pb$, $^{47}Sc$, $^{109}Pd$, $^{234}Th$, and $^{40}K$, $^{157}Gd$, $^{55}Mn$, $^{52}Tr$ and $^{56}Fe$.

The antibodies and antibody fragments or the MDL-1 soluble proteins or fragments thereof of the invention may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaldehyde, fluorescamine, $^{152}Eu$, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any method known in the art for conjugating the antibody molecules or protein molecules of the invention to the various moieties may be employed, including those methods described by Hunter et al., (1962) Nature 144:945; David et al., (1974) Biochemistry 13:1014; Pain et al., (1981) J. Immunol. Meth. 40:219; and Nygren, J., (1982) Histochem. and Cytochem. 30:407. Methods for conjugating antibodies and proteins are conventional and very well known in the art.

V. Biological Activity of Humanized Anti-MDL-1 Antibodies

Antibodies having the characteristics identified herein as being desirable in a humanized anti-MDL-1 antibody can be screened for inhibitory biologic activity in vitro or suitable binding affinity. Agonist antibodies may be distinguished from antagonist antibodies using the biological assay provided at Example 5. Antibodies that exhibit agonist activity will not block the activity of MDL-1 and/or DAP12, but will instead stimulate the response typically caused by MDL-1.

To screen for antibodies that bind to the epitope on human MDL-1 bound by an antibody of interest (e.g., those that block binding of MDL-1), a routine cross-blocking assay such as that described in ANTIBODIES, A LABORATORY MANUAL, Cold Spring Harbor Laboratory, Ed Harlow and David Lane (1988), can be performed. Antibodies that bind to the same epitope are likely to cross-block in such assays, but not all cross-blocking antibodies will necessarily bind at precisely the same epitope since cross-blocking may result from steric hindrance of antibody binding by antibodies bind at overlapping epitopes, or even nearby non-overlapping epitopes.

Alternatively, epitope mapping, e.g., as described in Champe et al. (1995) *J. Biol. Chem.* 270:1388-1394, can be performed to determine whether the antibody binds an epitope of interest. "Alanine scanning mutagenesis," as described by Cunningham and Wells (1989) *Science* 244: 1081-1085, or some other form of point mutagenesis of amino acid residues in human MDL-1 may also be used to determine the functional epitope for an anti-MDL-1 antibody of the present invention. Mutagenesis studies, however, may also reveal amino acid residues that are crucial to the overall three-dimensional structure of MDL-1 but that are not directly involved in antibody-antigen contacts, and thus other methods may be necessary to confirm a functional epitope determined using this method.

The epitope bound by a specific antibody may also be determined by assessing binding of the antibody to peptides comprising fragments of human MDL-1 (SEQ ID NO: 41). A series of overlapping peptides encompassing the sequence of MDL-1 may be synthesized and screened for binding, e.g. in a direct ELISA, a competitive ELISA (where the peptide is assessed for its ability to prevent binding of an antibody to MDL-1 bound to a well of a microtiter plate), or on a chip. Such peptide screening methods may not be capable of detecting some discontinuous functional epitopes, i.e. functional epitopes that involve amino acid residues that are not contiguous along the primary sequence of the MDL-1 polypeptide chain.

The epitope bound by antibodies of the present invention may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in MDL-1 when free and when bound in a complex with an antibody of interest (Zinn-Justin et al. (1992) *Biochemistry* 31:11335-11347; Zinn-Justin et al. (1993) *Biochemistry* 32:6884-6891).

With regard to X-ray crystallography, crystallization may be accomplished using any of the known methods in the art (e.g. Giege et al. (1994) *Acta Crystallogr.* D50:339-350; McPherson (1990) *Eur. J. Biochem.* 189:1-23), including microbatch (e.g. Chayen (1997) *Structure* 5:1269-1274), hanging-drop vapor diffusion (e.g. McPherson (1976) *J. Biol. Chem.* 251:6300-6303), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g. glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 3.0 to about 5.0, preferably about 4.0. Specific buffers useful in the precipitant solution may vary and are well-known in the art. Scopes, Protein Purification: Principles and Practice, Third ed., (1994) Springer-Verlag, New York. Examples of useful buffers include, but are not limited to, HEPES, Tris, MES and acetate. Crystals may be grow at a wide range of temperatures, including 2° C., 4° C., 8° C. and 26° C.

Antibody:antigen crystals may be studied using well-known X-ray diffraction techniques and may be refined using computer software such as X-PLOR (Yale University, 1992, distributed by Molecular Simulations, Inc.; see e.g. Blundell & Johnson (1985) *Meth. Enzymol.* 114 & 115, H. W. Wyckoff et al. eds., Academic Press; U.S. Patent Application Publication No. 2004/0014194), and BUSTER (Bricogne (1993) *Acta Cryst.* D49:37-60; Bricogne (1997) *Meth. Enzymol.* 276A:361-423, Carter & Sweet, eds.; Roversi et al. (2000) *Acta Cryst.* D56:1313-1323).

Additional antibodies binding to the same epitope as an antibody of the present invention may be obtained, for example, by screening of antibodies raised against MDL-1 for binding to the epitope, or by immunization of an animal with a peptide comprising a fragment of human MDL-1 comprising the epitope sequence. Antibodies that bind to the same functional epitope might be expected to exhibit similar biological activities, such as blocking receptor binding, and such activities can be confirmed by functional assays of the antibodies.

Antibody affinities may be determined using standard analysis. Preferred humanized antibodies are those that bind human MDL-1 with a $K_d$ value of no more than about $1\times10^{-7}$; preferably no more than about $1\times10^{-8}$; more preferably no more than about $1\times10^{-9}$; and most preferably no more than about $1\times10^{-10}$ or even $1\times10^{-11}$ M.

The antibodies and fragments thereof useful in the present compositions and methods are biologically active antibodies and fragments. As used herein, the term "biologically active" refers to an antibody or antibody fragment that is capable of binding the desired the antigenic epitope and directly or indirectly exerting a biologic effect. As used herein, the term "specific" refers to the selective binding of the antibody to the target antigen epitope. Antibodies can be tested for specificity of binding by comparing binding to MDL-1 to binding to irrelevant antigen or antigen mixture under a given set of conditions. If the antibody binds to MDL-1 at least 10, and preferably 50 times more than to irrelevant antigen or antigen mixture then it is considered to be specific. An antibody that "specifically binds" to MDL-1 does not bind to proteins that do not comprise the MDL-1-derived sequences, i.e. "specificity" as used herein relates to MDL-1 specificity, and not any other sequences that may be present in the protein in question. For example, as used herein, an antibody that "specifically binds" to a polypeptide comprising MDL-1 will typically bind to FLAG®-MDL-1, which is a fusion protein comprising MDL-1 and a FLAG® peptide tag, but it does not bind to the FLAG® peptide tag alone or when it is fused to a protein other than MDL-1.

MDL-1-specific binding compounds of the present invention, such as agonistic MDL-1 specific antibodies, can enhance its biological activity in any manner, including but not limited to increasing the immune response to a microbial infection.

VI. Pharmaceutical Compositions

To prepare pharmaceutical or sterile compositions including MDL-1 antibody, the cytokine analogue or mutein, antibody thereto, or nucleic acid thereof, is admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Formulations of therapeutic and diagnostic agents may be prepared by mixing with physiologically acceptable carriers, excipients, or stabilizers in the form of, e.g., lyophilized powders, slurries, aqueous solutions or suspensions. See, e.g., Hardman et al. (2001) *Goodman and* Gilman's *The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis et al. (eds.) (1993) *Pharmaceutical Dosage Forms Parenteral Medications*, Marcel Dekker, NY; Lieberman, et al. (eds.) (1990) *Pharmaceutical Dosage Forms: Tablets*, Marcel Dekker, NY; Lieberman et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.

Toxicity and therapeutic efficacy of the antibody compositions, administered alone or in combination with an immunosuppressive agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio of $LD_{50}$ to $ED_{50}$. Antibodies exhibiting high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

The mode of administration is not particularly important. Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of antibody used in the pharmaceutical composition or to practice the method of the present invention can be carried out in a variety of conventional ways, such as oral ingestion, inhalation, topical application or cutaneous, subcutaneous, intraperitoneal, parenteral, intraarterial or intravenous injection.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348: 601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is substantially derived from the same species as the animal targeted for treatment (e.g. a humanized antibody for treatment of human subjects), thereby minimizing any immune response to the reagent.

Antibodies, antibody fragments, and cytokines can be provided by continuous infusion, or by doses at intervals of, e.g., one day, 1-7 times per week, one week, two weeks, monthly, bimonthly, etc. Doses may be provided intravenously, subcutaneously, topically, orally, nasally, rectally, intramuscular, intracerebrally, intraspinally, or by inhalation. A preferred dose protocol is one involving the maximal dose or dose frequency that avoids significant undesirable side effects. A total weekly dose is generally at least 0.05 μg/kg, 0.2 μg/kg, 0.5 μg/kg, 1 μg/kg, 10 μg/kg, 100 μg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346: 1692-1698; Liu et al. (1999) *J. Neurol. Neurosurg. Psych.* 67:451-456; Portielji et al. (20003) *Cancer Immunol. Immunother.* 52:133-144. The desired dose of a small molecule therapeutic, e.g., a peptide mimetic, natural product, or organic chemical, is about the same as for an antibody or polypeptide, on a moles/kg basis.

As used herein, "inhibit" or "treat" or "treatment" includes a postponement of development of the symptoms associated with autoimmune disease or pathogen-induced immunopathology and/or a reduction in the severity of such symptoms that will or are expected to develop. The terms further include ameliorating existing uncontrolled or unwanted autoimmune-related or pathogen-induced immunopathology symptoms, preventing additional symptoms, and ameliorating or preventing the underlying causes of such symptoms. Thus, the terms denote that a beneficial result has been conferred on a vertebrate subject with an autoimmune or pathogen-induced immunopathology disease or symptom, or with the potential to develop such a disease or symptom.

As used herein, the term "therapeutically effective amount" or "effective amount" refers to an amount of an MDL-1-specific binding compound, e.g. and antibody, that when administered alone or in combination with an additional therapeutic agent to a cell, tissue, or subject is effective to prevent or ameliorate the autoimmune disease or pathogen-induced immunopathology associated disease or condition or the progression of the disease. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of therapeutic will decrease the symptoms typically by at least 10%; usually by at least 20%; preferably at least about 30%; more preferably at least 40%, and most preferably by at least 50%.

Methods for co-administration or treatment with a second therapeutic agent, e.g., a cytokine, antibody, steroid, chemotherapeutic agent, antibiotic, or radiation, are well known in the art, see, e.g., Hardman et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa. Antibiotics can include known antibacterial, anti-fungal, and anti-viral agents. Antibacterial agents can include, but are not limited to beta lactam agents that inhibit of cell wall synthesis, such as penicillins, cephalosporins, cephamycins, carbopenems, monobactam; and non beta lactam agents that inhibit cell wall synthesis, such as vancomycin and teicoplanin. Other antibiotics can inhibit cellular activity such as protein and nucleic acid synthesis. These agents include, but are not limited to, macrolides, tetracyclines, aminoglycosides, chloramphenicol, sodium fusidate, sulphonamides, quinolones, and azoles.

Known anti-fungals include, but are not limited to, allylamines and other non-azole ergosterol biosynthesis inhibitors, such as terbinafine; antimetabolites, such as flucytosine; azoles, such as fluconazole, itraconazole, ketoconazole, ravuconazole, posaconazole, and voriconazole; glucan synthesis inhibitors, such as caspofungin, micafungin, and anidulafungin; polyenes, such as amphotericin B, amphotericin B Lipid Complex (ABLC), amphotericin B colloidal dispersion (ABCD), liposomal amphotericin B (L-AMB), and liposomal nystatin; and other systemic agents, such as griseofulvin.

Anti-virals include any drug that destroys viruses. Antivirals may include interferons which function to inhibits replication of the virus, protease inhibitors, and reverse transcriptase inhibitors.

Typical veterinary, experimental, or research subjects include monkeys, dogs, cats, rats, mice, rabbits, guinea pigs, horses, and humans.

VII. Antibody Production

In one embodiment, for recombinant production of the antibodies of the present invention, the nucleic acids encoding the two chains are isolated and inserted into one or more replicable vectors for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence. In one embodiment, both the light and heavy chains of a humanized anti-MDL-1 antibody of the present invention are expressed from the same vector, e.g. a plasmid or an adenoviral vector.

Antibodies of the present invention may be produced by any method known in the art. In one embodiment, antibodies are expressed in mammalian or insect cells in culture, such as chinese hamster ovary (CHO) cells, human embryonic kidney (HEK) 293 cells, mouse myeloma NSO cells, baby hamster kidney (BHK) cells, *Spodoptera frugiperda* ovarian (Sf9) cells. In one embodiment, antibodies secreted from CHO cells are recovered and purified by standard chromatographic methods, such as protein A, cation exchange, anion exchange, hydrophobic interaction, and hydroxyapatite chromatography. Resulting antibodies are concentrated and stored in 20 mM sodium acetate, pH 5.5.

In another embodiment, the antibodies of the present invention are produced in yeast according to the methods described in WO2005/040395. Briefly, vectors encoding the individual light or heavy chains of an antibody of interest are introduced into different yeast haploid cells, e.g. different mating types of the yeast *Pichia pastoris*, which yeast haploid cells are optionally complementary auxotrophs. The transformed haploid yeast cells can then be mated or fused to give a diploid yeast cell capable of producing both the heavy and the light chains. The diploid strain is then able to secret the fully assembled and biologically active antibody. The relative expression levels of the two chains can be optimized, for example, by using vectors with different copy number, using transcriptional promoters of different strengths, or inducing expression from inducible promoters driving transcription of the genes encoding one or both chains.

In one embodiment, the respective heavy and light chains of a plurality of different anti-MDL-1 antibodies (the "original" antibodies) are introduced into yeast haploid cells to create a library of haploid yeast strains of one mating type expressing a plurality of light chains, and a library of haploid yeast strains of a different mating type expressing a plurality of heavy chains. These libraries of haploid strains can be mated (or fused as spheroplasts) to produce a series of diploid yeast cells expressing a combinatorial library of antibodies comprised of the various possible permutations of light and heavy chains. The combinatorial library of antibodies can then be screened to determine whether any of the antibodies has properties that are superior (e.g. higher affinity for MDL-1) to those of the original antibodies. See. e.g., WO2005/040395.

In another embodiment, antibodies of the present invention are human domain antibodies in which portions of an antibody variable domain are linked in a polypeptide of molecular weight approximately 13 kDa. See, e.g., U.S. Pat. Publication No. 2004/0110941. Such single domain, low molecular weight agents provide numerous advantages in terms of ease of synthesis, stability, and route of administration.

VIII. Uses

The present invention provides methods for using anti-MDL-1 antibodies and fragments thereof for the treatment and diagnosis of inflammatory disorders and conditions, e.g., infectious diseases and cancers.

The present invention provides methods for diagnosing the presence of a microbial infection or cancer by analyzing expression levels of MDL-1 in test cells, tissue or bodily fluids compared with MDL-1 levels in cells, tissues or bodily fluids of preferably the same type from a control. As demonstrated herein, an increase in level of MDL-1 expression, for example, in the patient versus the control is associated with the presence of cancer or microbial infection.

Typically, for a quantitative diagnostic assay, a positive result indicating the patient tested has cancer or an infectious disease, is one in which the cells, tissues, or bodily fluids has an MDL-1 expression level at least two times higher, five times higher, ten times higher, fifteen times higher, twenty times higher, twenty-five times higher.

Assay techniques that may be used to determine levels of gene and protein expression, such as MDL-1, of the present inventions, in a sample derived from a host are well known to those of skill in the art. Such assay methods include radioimmunoassays, reverse transcriptase PCR (RT-PCR) assays, quantitative real-time PCR assays, immunohistochemistry assays, in situ hybridization assays, competitive-binding assays, western blot assays, ELISA assays, and flow cytometric assays, for example, two color FACS analysis for M2 versus M1 phenotyping of tumor-associated macrophages (Mantovani et al., (2002) TRENDS in Immunology 23:549-555).

An ELISA assay initially comprises preparing an antibodies of the present invention, specific to MDL-1, preferably DX230, DX241, DX244, DX246, and DX297 (collectively "MDL-1 antibodies"). In addition, a reporter antibody generally is prepared that binds specifically to MDL-1. The reporter antibody is attached to a detectable reagent such as radioactive, fluorescent or an enzymatic reagent, for example horseradish peroxidase enzyme or alkaline phosphatase.

To carry out the ELISA, at least one of the MDL-1 antibodies described above is incubated on a solid support, e.g., a polystyrene dish that binds the antibody. Any free protein binding sites on the dish are then covered by incubating with a non-specific protein, such as bovine serum albumin. Next, the sample to be analyzed is incubated in the dish, during which time MDL-1 binds to the specific MDL-1 antibody attached to the polystyrene dish. Unbound sample is washed out with buffer. A reporter antibody specifically directed to MDL-1 and linked to horseradish peroxidase is placed in the dish resulting in binding of the reporter antibody to any monoclonal antibody bound to MDL-1. Unattached reporter antibody is then washed out. Reagents for peroxidase activity, including a calorimetric substrate are then added to the dish. Immobilized peroxidase, linked to MDL-1 antibodies, produces a colored reaction product. The amount of color developed in a given time period is proportional to the amount of MDL-1 protein present in the sample. Quantitative results typically are obtained by reference to a standard curve.

A competition assay may be employed wherein antibodies specific to MDL-1 are attached to a solid support and labeled MDL-1 and a sample derived from the host are passed over the solid support and the amount of label detected attached to the solid support can be correlated to a quantity of MDL-1 in the sample.

The above tests may be carried out on samples derived from a variety of cells, bodily fluids and/or tissue extracts such as homogenates or solubilized tissue obtained from a patient. Tissue extracts are obtained routinely from tissue biopsy and autopsy material. Bodily fluids useful in the present invention include blood, urine, saliva or any other bodily secretion or derivative thereof. The term "blood" is meant to include whole blood, plasma, serum or any derivative of blood.

The broad scope of this invention is best understood with reference to the following examples, which are not intended to limit the inventions to the specific embodiments. The specific embodiments described herein are offered by way of example only, and the invention is to be limited by the terms of the appended claims, along with the full scope of equivalents to which such claims are entitled.

EXAMPLES

Example 1

General Methods

Standard methods in molecular biology are described. Maniatis et al. (1982) *Molecular Cloning, A Laboratory Manual*, Cold Spring Harbor Laboratory Press, Cold Spring Harbor, N.Y.; Sambrook and Russell (2001) *Molecular Cloning, 3rd ed.*, Cold Spring Harbor Laboratory Press, Cold Spring Harbor, N.Y.; Wu (1993) *Recombinant DNA*, Vol. 217, Academic Press, San Diego, Calif. Standard methods also appear in Ausbel et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described. Coligan et al. (2000) *Current Protocols in Protein Science*, Vol. 1, John Wiley and Sons, Inc., New York. Chemical analysis, chemical modification, post-translational modification, production of fusion proteins, glycosylation of proteins are described. See, e.g., Coligan et al. (2000) *Current Protocols in Protein Science*, Vol. 2, John Wiley and Sons, Inc., New York; Ausubel et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391. Production, purification, and fragmentation of polyclonal and monoclonal antibodies are described. Coligan et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra. Standard techniques for characterizing ligand/receptor interactions are available. See, e.g., Coligan et al. (2001) *Current Protocols in Immunology*, Vol. 4, John Wiley, Inc., New York.

Methods for flow cytometry, including fluorescence activated cell sorting detection systems (FACS®), are available. See, e.g., Owens et al. (1994) *Flow Cytometry Principles for Clinical Laboratory Practice*, John Wiley and Sons, Hoboken, N.J.; Givan (2001) *Flow Cytometry, 2nd ed.*; Wiley-Liss, Hoboken, N.J.; Shapiro (2003) *Practical Flow Cytometry*, John Wiley and Sons, Hoboken, N.J. Fluorescent reagents suitable for modifying nucleic acids, including nucleic acid primers and probes, polypeptides, and antibodies, for use, e.g., as diagnostic reagents, are available. Molecular Probes (2003) *Catalogue*, Molecular Probes, Inc., Eugene, Oreg.; Sigma-Aldrich (2003) *Catalogue*, St. Louis, Mo.

Standard methods of histology of the immune system are described. See, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.

Software packages and databases for determining, e.g., antigenic fragments, leader sequences, protein folding, functional domains, glycosylation sites, and sequence alignments, are available. See, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne et al. (2000) *Bioinformatics* 16: 741-742; Menne et al. (2000) *Bioinformatics Applications Note* 16:741-742; Wren et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690.

Example 2

Humanization of Anti-Human MDL-1 Antibodies

The humanization of antibodies is described generally, e.g., in PCT patent application publications WO 2005/047324 and WO 2005/047326.

Briefly, the amino acid sequence of the non-human VH domain (e.g. SEQ ID NOs: 1-5) is compared to a group of five human VH germline amino acid sequences; one representative from subgroups IGHV1 and IGHV4 and three representatives from subgroup IGHV3. The VH subgroups are listed in M.-P. Lefranc (2001) "Nomenclature of the Human Immunoglobulin Heavy (IGH) Genes", *Experimental and Clinical Immunogenetics* 18:100-116. The framework sequences of the human germline sequence with the closest match are used to construct a humanized VH domain.

The rodent anti-huMDL-1 antibodies disclosed herein are all of the kappa subclass of VL. The amino acid sequences of the non-human VL domain (e.g. SEQ ID NOs: 6-10) is compared to a group of four human VL kappa germline amino acid sequences. The group of four is comprised of one representative from each of four established human VL subgroups listed in V. Barbie & M.-P. Lefranc (1998) "The Human Immunoglobulin Kappa Variable (IGKV) Genes and Joining (IGKJ) Segments", *Experimental and Clinical Immunogenetics* 15:171-183 and M.-P. Lefranc (2001) "Nomenclature of the Human Immunoglobulin Kappa (IGK) Genes", *Experimental and Clinical Immunogenetics* 18:161-174. The four subgroups also correspond to the four subgroups listed in Kabat et al. (1991-5th Ed.) "Sequences of Proteins of Immunological Interest", U.S. Department of Health and Human Services, NIH Pub. 91-3242, pp. 103-130. The framework sequences of the human germline sequence with the closest match are used to construct a humanized VL domain.

Once the target amino acid sequences of the variable heavy and light chains are determined, plasmids encoding the full-length humanized antibody may be generated. Plasmid sequences may be altered using Kunkel mutagenesis (see, e.g., Kunkel T A. (1985) Proc. Natl. Acad. Sci. U.S.A. 82:488-492) to change the DNA sequence to the target humanized antibody sequences. Simultaneously, codon optimization may be performed to provide for potentially optimal expression.

Example 3

Determining the Equilibrium Dissociation Constant ($K_d$) for Anti-Human MDL-1 Antibodies Using KinExA Technology The equilibrium dissociation constants ($K_d$) for anti human MDL-1 antibodies are determined using the KinExA 3000 instrument. Sapidyne Instruments Inc., Boise Id., USA. KinExA uses the principle of the Kinetic Exclusion Assay method based on measuring the concentration of uncomplexed antibody in a mixture of antibody, antigen and antibody-antigen complex. The concentration of free antibody is measured by exposing the mixture to a solid-phase immobilized antigen for a very brief period of time. In practice, this is accomplished by flowing the solution phase antigen-antibody mixture past antigen-coated particles trapped in a flow cell. Data generated by the instrument are analyzed using custom software. Equilibrium constants are calculated using a mathematical theory based on the following assumptions:

1. The binding follows the reversible binding equation for equilibrium:

$$k_{on}[Ab][Ag] = k_{off}[AbAg]$$

2. Antibody and antigen bind 1:1 and total antibody equals antigen-antibody complex plus free antibody.

3. Instrument signal is linearly related to free antibody concentration.

PMMA particles (Sapidyne, Cat No. 440198) are coated with biotinylated MDL-1 (or a fragment thereof, such as the extracellular domain) according to Sapidyne "Protocol for coating PMMA particles with biotinylated ligands having short or nonexistent linker arms." EZ-link TFP PEO-biotin (Pierce, Cat. No. 21219) is used for biotinylation of MDL-1, as per the manufacturer's recommendations (Pierce bulletin 0874).

Example 4

Determining the Equilibrium Dissociation Constant ($K_d$) for Humanized Anti-Human MDL-1 Antibodies Using BIAcore Technology BIAcore determinations are performed essentially as described at Example 4 of co-pending, commonly assigned U.S. patent application Ser. No. 11/511,635 (filed 29 Aug. 2006). Briefly, ligands (anti-MDL-1-hIg) are immobilized on a BIAcore CM5 sensor chip using standard amine-coupling procedure. Kinetic constants for the various interactions are determined using BIAevaluation software 3.1. The $K_d$ is determined using the calculated dissociation and association rate constants.

Antibodies DX230, DX241, DX244, DX246, DX233, DX239, and DX240 had the following Kd values:

TABLE 4

Affinity measurements of MDL-1 antibodies

| Analyte (mAb) | Capture antigen | ka (1/Ms) ($\times 10^5$) | kd (1/s) ($\times 10^{-6}$) | Apparent Kd (pM) |
|---|---|---|---|---|
| DX230 | hMDL-1-hIG | 0.63 | 1602 | 25248 |
| DX241 | hMDL-1-hIG | 3.54 | 73 | 207 |
| DX244 | hMDL-1-hIG | 2.77 | 68 | 247 |
| DX246 | hMDL-1-hIG | 6.44 | 817 | 1268 |

For antibodies DX233, DX239, and DX240, the antibodies were used as the capture reagent and the MDL-1-hIg ligand was used as the analyte. Affinity measurements for DX233, DX239, and DX240 were as follows.

TABLE 5

Affinity measurements of MDL-1 antibodies (DX233, DX239, and DX240)

| Analyte ligand | Capture mAb | ka (1/Ms) ($\times 10^5$) | kd (1/s) ($\times 10^{-6}$) | Apparent Kd (pM) |
|---|---|---|---|---|
| hMDL-1-hIG | DX233 | 0.20 | 147 | 8647 |
| hMDL-1-hIG | DX239 | 0.10 | 336 | 37910 |
| hMDL-1-hIG | DX240 | 0.08 | 325 | 43046 |

Example 5

Humanization of DX239 and DX244

Antibodies of the present invention can be humanized using a method that identifies an acceptor germline sequence for a humanized antibody, and comprises the steps of: a) identifying a non-human antibody that has the desired biological activity; b) determining the amino acid sequence of a non-human antibody $V_H$ and $V_L$ domains; and c) comparing the nonhuman antibody sequence to a group of human germline sequences, wherein the comparison comprises the sub-steps of: 1) assigning the non-human V sequences residue numbers according to Kabat supra; 2) delineating the CDR and FR regions in the sequence according to Kabat supra; 3) assigning a predetermined numerical score at specific residue position for which the non-human and human antibody germline sequences are identical; and 4) totaling all of the residue scores to generate a total score for each human germline sequence; and d) identifying the human germline sequence with the highest total residue score as the acceptor germline sequence. In one embodiment, the method further comprises the substeps of: 5) assigning a numerical score of 1 for each FR residue position for which the non-human and human antibody germline sequences are identical that was not scored in substep (3) to germline sequences with identical total residue scores after substep (4); 6) totaling all of the residue scores to generate a total score for each human germline sequence. In a specific embodiment, the non-human antibody is specific for MDL-1 and inhibits the biological activity of MDL-1. Also provided herein is an antibody generated by the above method.

In one embodiment, the MDL-1 antibody is humanized using the following method. First, the non-human $V_L$ and $V_H$ domains of the MDL-1 antibody are cloned and sequenced, and the amino acid sequence determined. Then, the non-human $V_H$ sequence are compared to a group of three human $V_H$ germline amino acid sequences. The three groups contain one representative from each of subgroups IGHV1, IGHV3 and IGHV4. The $V_H$ subgroups are listed in M.-P. Lefranc,

*Exp. Clin. Immunogenetics,* 18:100-116 (2001). Specifically, the comparison with the three germline sequences begins with the assignment of residue numbers to the non-human $V_H$ sequence according to the Kabat numbering system. See Kabat, et al., U.S. Department of Health and Human Services, NIH Pub. 91-3242 (5th Ed., 1991). The non-human $V_H$ sequence are then aligned with each of the three human germline sequences. Since the V genes only comprise $V_H$ residues 1-94, only these residues are considered in the alignment. Next, the complementarity-determining (CDR) and framework (FR) regions in the sequence are delineated. CDR and FR are delineated according to the combination of the definitions provided in Kabat, et al., U.S. Department of Health and Human Services, NIH Pub. 91-3242 (5th Ed., 1991), and C. Chothia & A. M. Lesk, *J. Mol. Biol.,* 196:901-917 (1987). Therefore, the CDR definition used is residues 26-35 for CDR1, residues 50-65 for CDR2, and CDR3 is residues 95-102 for CDR3 of the $V_H$ domain. The next step involves assigning a numerical score at identified residue position where the non-human and human sequences are identical. One example of this scoring is shown in Table 6 below.

TABLE 6

| Residue # | Score | Reason |
|---|---|---|
| 24 | 3 | Affects CDR-H1 |
| 27 | 4 | Affects CDR-H1, 3* |
| 29 | 4 | Affects CDR-H1* |
| 34 | 4 | Affects CDR-H1* |
| 35 | 2 | VH/VL interface |
| 37 | 2 | VH/VL interface |
| 48 | 3 | Affects CDR-H2 |
| 49 | 3 | Affects CDR-H2 |
| 50 | 2 | VH/VL interface |
| 58 | 2 | VH/VL interface |
| 60 | 2 | VH/VL interface |
| 63 | 3 | Affects CDR-H2 |
| 67 | 3 | Affects CDR-H2 |
| 69 | 3 | Affects CDR-H2 |
| 71 | 4 | Affects CDR-H2* |
| 73 | 3 | Affects CDR-H1 |
| 76 | 3 | Affects CDR-H1 |
| 78 | 3 | Affects CDR-H1 |
| 94 | 4 | Affects CDR-H3* |
| max | 57 | |

*Noted as affecting CDR conformation in C. Chothia et al., *Nature* 342:877-883, (1989).

After the residue positions are assigned a numerical score, all of the residue scores are totaled. The acceptor germline sequence is the one with the highest total score. In a case where two or more germline sequences have identical scores, then add 1 to the total for each position where the non-human and human sequences are IDENTICAL for the following FR residues: 1-23, 25, 36, 38-47, 66, 68, 70, 72, 74, 75, 77, and 79-93 (max 60). The residue scores are totaled again, and the acceptor germline sequence is the one with the highest total score. If two or more germline sequences still have identical scores, either one can be used as the acceptor germline sequence.

If the $V_L$ sequence is a member of the kappa subclass of $V_L$, the non-human $V_L$ sequence from the MDL-1 specific antibody is compared to a group of four human $V_L$ kappa germline amino acid sequences. The four sequences are comprised of one representative from each of four established human $V_L$ subgroups listed in V. Barbie & M.-P. Lefranc, *Exp. Clin. Immunogenetics* 15:171-183 (1998) and M.-P. Lefranc, *Exp. Clin. Immunogenetics* 18:161-174 (2001). The four sequences also correspond to the four subgroups listed in Kabat et al., U.S. Department of Health and Human Services, NIH Pub. 91-3242, pp. 103-130 (5th Ed., 1991). The comparison of the non-human sequence to the four germline sequences begins with the assignment of residue numbers to the non-human $V_L$ sequence residues according to Kabat et al., U.S. Department of Health and Human Services, NIH Pub. 91-3242 (5th Ed., 1991). The non-human $V_L$ sequences are then aligned with each of the four human germline sequences. Since the V genes only comprise $V_L$ residues 1-95, only these residues are considered in the alignment. Next, the complementarity-determining (CDR) and framework (FR) regions are delineated in the sequence. CDR and FR are delineated according to the combination of the definitions provided in Kabat et al., U.S. Department of Health and Human Services, NIH Pub. 91-3242 (5th Ed. 1991), and C. Chothia & A. M. Lesk, *J. Mol. Biol.,* 196:901-917 (1987). Therefore, the CDR definition used is residues 24-34 for CDR1, residues 50-56 for CDR2, and residues 89-97 for CDR3 of the $V_L$ domain. The next step involves assigning a numerical score at identified residue position where the non-human and human sequences are identical. One example of this scoring is shown in Table 7 below.

TABLE 7

| Residue # | Score | Reason |
|---|---|---|
| 2 | 4 | Affects CDR-L1, 3* |
| 25 | 4 | Affects CDR-L1* |
| 29 | 4 | Affects CDR-L1, 3* |
| 34 | 2 | VL/VH interface |
| 43 | 2 | VL/VH interface |
| 55 | 2 | VL/VH interface |
| 58 | 3 | Affects CDR-L2 |
| 89 | 2 | VL/VH interface |
| 91 | 2 | VL/VH interface |
| 94 | 2 | VL/VH interface |
| max | 27 | |

*Noted as affecting CDR conformation in C. Chothia et al., *Nature* 342:877-883, (1989).

After the residue positions are assigned a numerical score, all of the residue scores are totaled. The acceptor germline sequence is the one with the highest total score. In a case where two or more germline sequences have identical scores, then add 1 to the total for each position where the non-human and human sequences are IDENTICAL for the following FR residues: 1-3, 5-23, 35-42, 44-49, 57, 59-88 (max 67). The residue scores are totaled again, and the acceptor germline sequence is the one with the highest total score. If two or more germline sequences still have identical scores, either one can be used as the acceptor germline sequence.

The humanization of the anti-human MDL-1 antibodies, DX239, was performed as described supra. FIG. 1 shows the assignment of residue numbers and corresponding numerical scores for residue positions that are identical to the germline sequences being examined. Calculations are shown for the variable regions of the light (FIG. 5A) and heavy (FIG. 5B) chains of the DX239 anti-human MDL-1 antibody and for the variable regions of the light (FIG. 5C) and heavy (FIG. 5D) chains of the DX244 anti-human MDL-1 antibody.

Example 6

Bioassays for the Assessment of Activating Anti-MDL-1 Antibodies

The ability of a monoclonal antibody to biologically enhance MDL-1/DAP12 activity was assessed by a mast cell degranulation assay.

Murine mast cell cultures were established from 2-3 week old C57BL/6 mice. Bone marrow was flushed from the femurs of 2-3 mice and subsequently washed three times with phosphate buffered saline (PBS). Cells were resuspended in 15 ml Dulbecco's minimal essential media (MEM) supplemented with sodium pyruvate, non-essential amino acids, 2-mercaptoethanol, N-2-hydroxyethylpiperazine-N'-2-ethanesulfonic acid (HEPES), glutamine, 10-15% fetal calf serum (Hyclone, Inc., Logan, Utah), 100 ng/mg rSCF, and 100 ng/ml of rIL-3. Cells were incubated in T25 flasks at 37° C. At weekly intervals, the non-adherent cells were refed with fresh media and transferred to a new flask. At two weeks, culture media was supplemented with 5.0 ng/ml of IL-4. By four weeks, the majority of non-adherent cells are expected to be typical murine mast cells expressing IgE FcR. From four weeks on, the cells were maintained with supplements of only rIL-3 and rIL-4.

Mouse mast cells were transfected with human MDL-1 (DT808) and stimulated with 1 μg/ml monoclonal antibody, followed by measurement of secreted β-hexosaminidase at 1.0 hours. Control cell incubations were conducted with the rat isotype control mAb (rIgG1; negative control) and DX87 and DX89, two anti-mCD200R antibodies as positive controls. DX87 requires cross-linking for function. After supernatant was taken for β-hexosaminidase measurement, a cross-linking antibody was added. 1 hour later supernatant was again assessed for β-hexosaminidase.

The results demonstrated that treatment with eight of the anti-MDL-1 antibodies enhanced mast cell degranulation. One mAb, DX245, required cross-linking for function. Negative control isotype antibodies did not detectably influence secretion. A similar degranulation bioassay was performed with human neutrophils, in which the increase in surface expression of CD11b and CD66b was measured in response to a subset of the anti-MDL-1 antibodies (see Table 10).

Example 7

L-Selectin Shedding Assay

Circulating bloodstream neutrophils express L-selectin (CD62L), which mediates neutrophil interaction with endothelial cell molecules and can be shed from activated neutrophils. It was therefore investigated whether certain MDL-1 antibodies described above trigger L-selectin shedding. Neutrophils were purified from peripheral blood of healthy donors by dextran sedimentation, hypotonic lysis of erythrocytes, and centrifugation through Ficoll-Hypaque, as described previously (Badwey et al. (1982) *Biochem Biophys Res Commun.* 106:170-174).

For MDL-1 activation, freshly isolated neutrophils, resuspended at $10^7$ cells/ml in RPMI 1640 with 10% of fetal calf serum, were incubated with anti-MDL-1 antibodies (10 μg/ml) or isotype control IgG1 for 1 h at 37° C. and 5% $CO_2$ in 96-well plates (Nunc, Denmark). After two washes with RPMI, cell-bound anti-hMDL-1 antibodies were cross-linked with 9 μg/ml of F(ab')$_2$ fragment goat anti-mouse IgG (H+L) antibody for 30 min at 37° C. and 5% $CO_2$. Cells were then washed twice and incubated with 20 μg/ml of chrompure mouse IgG antibody for 20 min at 4° C. to block unbound cross-linking antibody.

Untreated or stimulated cells ($10^7$ cells/ml) were resuspended in PBS containing 2 mM EDTA and 0.5% BSA. To measure changes in the surface expression of L-selectin, the cells were incubated with PE-conjugated anti-CD62L antibody (BD Bioscience, San Jose, Calif.) (2 μg/ml) for 30 min at 4° C.

After two washes, the samples were analyzed on a FACSCalibur flow cytometry (BD Biosciences). Data were analyzed using CellQuest Pro Software (BD Biosciences).

Table 11 shows a decrease of CD62L staining (Mean Fluorescent Intensity; MFI) of neutrophils treated with anti-MDL-1 antibodies (MFI calculated by isotype control treatment minus anti-hMDL-1 treatment).

TABLE 8

Anti-MDL-1 induced degranulation of DT808 mouse mast cells

|  | rIgG1 | DX230 | DX297 | DX241 | DX244 | DX245 | DX246 | DX87 | DX89 |
|---|---|---|---|---|---|---|---|---|---|
| No cross-link | 1.139 | 3.320 | 3.168 | 2.664 | 3.462 | 1.134 | 3.393 | 1.062 | 3.441 |
| Standard deviation | 0.071 | 0.0097 | 0.0154 | 0.0126 | 0.0476 | 0.0106 | 0.0276 | 0.037 | 0.098 |
| cross-link | 0.349 | 3.175 | 3.284 | 3.246 | 3.362 | 3.339 | 3.232 | 3.397 | 2.666 |
| standard deviation | 0.067 | 0.0048 | 0.0787 | 0.0886 | 0.0182 | 0.0742 | 0.0631 | 0.113 | 0.061 |

Values are ODs (405-570). DX87 & DX89 are positive, anti-mCD200R mAbs as controls

TABLE 9

DX233, DX239, and DX240 degranulation of DT808 mouse mast cells

|  | rIgG1 | DX233 | DX239 | DX240 |
|---|---|---|---|---|
| No cross-link | 0.100 | 1.222 | 1.004 | 1.832 |
| cross-link | 0.065 | 3.212 | 3.139 | 3.248 |

Values are ODs (405-570).

TABLE 10

Degranulation of CD11b+ human neutrophils and CD66b+ human neutrophils

|  | DX233 | DX239 | DX240 | DX244 | DX246 |
|---|---|---|---|---|---|
| CD11b+ | 302.7 +/− 123.1 | 377.0 +/− 72.4 | 336.0 +/− 58.1 | 348.8 +/− 46.1 | 392.8 +/− 37.4 |
| CD66b+ | 90.5 +/− 21.3 | 106.8 +/− 38.2 | 97.0 +/− 41.4 | 109.8 +/− 44.2 | 108.9 +/− 46.2 |

(Values represent increases in Mean Fluorescent Intensity as compared to isotype control treatment; n = 3 or 4)

TABLE 11

MDL-1 antibody induced shedding of neutrophil expressed L-selectin (CD62L)

| | DX233 | DX239 | DX240 | DX244 | DX26 |
|---|---|---|---|---|---|
| CD65L | 96.9 +/− 6.3 | 142.5 +/− 54.5 | 113.5 +/− 42.4 | 140.2 +/− 44.7 | 151.8 +/− 52.7 |

Example 8

Cecal Ligation and Punction (CLP) Model

A midline incision of 10-12 mm was made on anesthetized seven week old C57BL/6J mice, and cecums exposed. The cecums were ligated at approximately 10-12 mm from the distal end. The ligated cecums were then punctured with 19-27 gauge needles and survival assessed. It was initially found that punctures with 19 gauge needles yielded the most dramatic sepsis type conditions.

Another set of CLP mice (7-11 weeks of age) were generated as described above. Three groups were treated as follows:

TABLE 12

Anti-MDL-1 treatment of CLP mice

| Group | Treatment (subcutaneous injection) | Number of Mice | Duration |
|---|---|---|---|
| A | 500 µgs of isotype control or 500 µgs of DX163 (rat anti-mouse MDL-1 agonist antibody) | 15 | 10 days |
| B | 500 µgs of isotype control or 500 µgs of DX163 | 14 | 14 days |
| C | 800 µgs of isotype control or 800 µgs of DX163 | 20 | 20 days |

Table 13 shows the results of the above treatments. N/D=not determined

TABLE 13

| Group | Day | Percent Survival - isotype control | Percent Survival - DX163 treatment |
|---|---|---|---|
| A | 0 | 100 | 100 |
| | 1 | 40 | 67 |
| | 2 | 13 | 60 |
| | 3 | N/D | 47 |
| | 5 | N/D | 40 |
| | 10 | 13 | 40 |
| B | 0 | 100 | 100 |
| | 1 | 92 | 93 |
| | 2 | 50 | N/D |
| | 5 | N/D | 86 |
| | 13 | 50 | 86 |
| C | 0 | 100 | 100 |
| | 1 | 70 | N/D |
| | 2 | 45 | 90 |
| | 4 | N/D | 85 |
| | 6 | 40 | N/D |
| | 7 | 30 | N/D |
| | 10 | N/D | 80 |
| | 20 | 30 | 80 |

Example 9

Measurement of Bacteremia and Weight in CLP Mice

Blood was collected from a total of 10 mice 24 hours post CLP (5 mice from isotype control treatment and 5 ice from DX163 treatment. Serial dilutions were plated onto blood agar places and incubated overnight at 37° C. Colonies were counted. Mice were weighed every 24 hours after CLP.

TABLE 14

Bacteremia 24 hours post CLP

| Treatment | Mouse Number | CFU/mL of Blood |
|---|---|---|
| Isotype Control | 1 | $8.9 \times 10^6$ |
| | 2 | $>1.0 \times 10^7$ |
| | 3 | $1.1 \times 10^5$ |
| | 4 | $1.3 \times 10^5$ |
| | 5 | $1.5 \times 10^6$ |
| DX163 | 6 | 0 |
| | 7 | $7.3 \times 10^4$ |
| | 8 | 0 |
| | 9 | 0 |
| | 10 | 0 |

FIG. 6 shows weight measurements of post CLP mice.

Example 10

Reduction of S. aureus Bacterial Burden

*Staphylococcus aureus* is a Gram-positive extracellular bacterium and an important human pathogen that causes soft tissue and bloodborne infections, and pneumonia. The incidence of severe *S. aureus* infections is increasing, often as a result of methicillin-resistant strains of the organism (MRSA). The Center for Disease Control and Prevention recently estimated that 94,000 serious infections and 18,000 deaths occurred in the US in 2005 due to MRSA (Klevens et al., JAMA, 2007, 298:1763-1771).

Based on the finding that MDL-1 antibodies can enhance antimicrobial functions of human neutrophils, it was determined if an activating anti-mMDL-1 antibody (DX163) could affect the bacterial load in a murine model of *S. aureus* pneumonia. The model was established as described, e.g., by Wardenburg et al. (2007) *Infection and Immunity* 75:1040-1044. The infection dose was in the range $1\text{-}5 \times 10^8$ colony forming units (CFU) of *S. aureus* ATCC 27217, as detailed in the Tables. In a preventive setting, mice were dosed subcutaneously with isotype control or DX163 antibody either 2 or 12 hours prior to infection (Tables 15 and 16). In a therapeutic setting, mice were dosed with control or DX163 antibody intravenously 2 hours after infection (Table 17). Either 24 or 48 hours after infection, lungs were excised from euthanized mice and analyzed for total lung CFU by homogenization, serial dilution and plating. Administration of DX163 consistently reduced the lung bacterial burden compared to isotype control-treated mice.

TABLE 15

S. aureus pneumonia model - preventive treatment (−12 h dosing)

| Lung sampling time | 48 h post-infection |
|---|---|
| MAb dosing relative | −12 h |

TABLE 15-continued

S. aureus pneumonia model - preventive treatment (−12 h dosing)

| to infection | |
|---|---|
| Isotype control | 613281 |
| DX163 - anti-mMDL-1 | 112 |

Infection dose: $5 \times 10^8$ CFU S. aureus ATCC 27217
1 mg mAb s.c. 12 h pre-infection
Values are mean CFU from whole lung ($n \geq 4$)

TABLE 16

S. aureus pneumonia model - preventive treatment (−2 and −12 h dosing)

| Lung sampling time | 24 h post-infection | | 48 h post-infection | |
|---|---|---|---|---|
| MAb dosing relative to infection | −12 h | −2 h | −12 h | −2 h |
| Isotype control | 883575 | 1105000 | 20667 | 10620 |
| DX163 - anti-mMDL-1 | 19425 | 30600 | 960 | 435 |

Infection dose: $1 \times 10^8$ CFU S. aureus ATCC 27217
1 mg mAb s.c. 12 h or 2 h pre-infection
Values are mean CFU from whole lung at either 24 h or 48 h post-infection ($n \geq 3$)

TABLE 17

S. aureus pneumonia model - therapeutic treatment (+2 h dosing)

| Lung sampling time | 48 h post-infection |
|---|---|
| MAb dosing relative to infection | +2 h |
| Isotype control | 202780 |
| DX163 - anti-mMDL-1 | 858 |

Infection dose: $1.5 \times 10^8$ CFU S. aureus ATCC 27217
1 mg mAb i.v. 12 h pre-infection
Values are mean CFU from whole lung ($n \geq 3$)

TABLE 18

Sequence Identifiers

| SEQ ID NO.: | Description |
|---|---|
| 1 | DX230 Heavy Chain Variable |
| 2 | DX241 Heavy Chain Variable |
| 3 | DX244 Heavy Chain Variable |
| 4 | DX246 Heavy Chain Variable |
| 5 | DX297 Heavy Chain Variable |
| 6 | DX233 Heavy Chain Variable |
| 7 | DX239 Heavy Chain Variable |
| 8 | DX240 Heavy Chain Variable |
| 9 | DX230 Light Chain Variable |
| 10 | DX241 Light Chain Variable |
| 11 | DX244 Light Chain Variable |
| 12 | DX246 Light Chain Variable |
| 13 | DX297 Light Chain Variable |
| 14 | DX233 Light Chain Variable |
| 15 | DX239 Light Chain Variable |
| 16 | DX240 Light Chain Variable |
| 17 | DX230 CDRH1 |
| 18 | DX241 CDRH1 |
| 19 | DX244 CDRH1 |
| 20 | DX246 CDRH1 |
| 21 | DX297 CDRH1 |
| 22 | DX233 CDRH1 |
| 23 | DX239 CDRH1 |
| 24 | DX240 CDRH1 |
| 25 | DX230 CDRH2 |
| 26 | DX241 CDRH2 |
| 27 | DX244 CDRH2 |
| 28 | DX246 CDRH2 |
| 29 | DX297 CDRH2 |
| 30 | DX233 CDRH2 |
| 31 | DX239 CDRH2 |
| 32 | DX240 CDRH2 |
| 33 | DX230 CDRH3 |
| 34 | DX241 CDRH3 |
| 35 | DX244 CDRH3 |
| 36 | DX246 CDRH3 |
| 37 | DX297 CDRH3 |
| 38 | DX233 CDRH3 |
| 39 | DX239 CDRH3 |
| 40 | DX240 CDRH3 |
| 41 | DX230 CDRL1 |
| 42 | DX241 CDRL1 |
| 43 | DX244 CDRL1 |
| 44 | DX246 CDRL1 |
| 45 | DX297 CDRL1 |
| 46 | DX233 CDRL1 |
| 47 | DX239 CDRL1 |
| 48 | DX240 CDRL1 |
| 49 | DX230 CDRL2 |
| 50 | DX241 CDRL2 |
| 51 | DX244 CDRL2 |
| 52 | DX246 CDRL2 |
| 53 | DX297 CDRL2 |
| 54 | DX233 CDRL2 |
| 55 | DX239 CDRL2 |
| 56 | DX240 CDRL2 |
| 57 | DX230 CDRL3 |
| 58 | DX241 CDRL3 |
| 59 | DX244 CDRL3 |
| 60 | DX246 CDRL3 |
| 61 | DX297 CDRL3 |
| 62 | DX233 CDRL3 |
| 63 | DX239 CDRL3 |
| 64 | DX240 CDRL3 |
| 65 | Human MDL-1 |
| 66 | Human DAP 12 |
| 67 | Humanized DX239 VH domain |
| 68 | Humanized DX244 VH domain |
| 69 | Humanized DX239 VL domain |
| 70 | Humanized DX244 VL domain |
| 71 | Human Z-012 VL germline |
| 72 | Human Z-A19 VL germline |
| 73 | Human Z-A27 VL germline |
| 74 | Human Z-B3 VL germline |
| 75 | Human DP-14 VH germline |
| 76 | Human DP-46 VH germline |
| 77 | Human DP-71 VH germline |

What is claimed is:

1. A binding compound that binds to human MDL-1 comprising:
   a) a light chain variable domain, or antigen binding fragment thereof, having a CDRL1 of SEQ ID NO: 43, a CDRL2 of SEQ ID NO: 51, and a CDRL3 of SEQ ID NO: 59; and
   b) a heavy chain variable domain, or antigen binding fragment thereof, having a CDRH1 of SEQ ID NO: 19, a CDRH2 of SEQ ID NO: 27; and a CDRH3 of SEQ ID NO: 35.

2. The binding compound of claim 1, wherein:
   a) the light chain variable domain comprises the sequence of SEQ ID NO: 11; and
   b) the heavy chain variable domain comprises the sequence of SEQ ID NO: 3.

3. The binding compound of claim 1, wherein the binding compound is an antibody fragment selected from the group consisting of Fab, Fab', Fab'-SH, Fv, scFv, F(ab')$_2$, and a diabody.

4. The binding compound of claim 1, wherein the binding compound is a monoclonal antibody.

5. The monoclonal antibody of claim 4, wherein the monoclonal antibody comprises an antibody secreted by a hybridoma deposited with the ATCC as accession number PTA-8375.

6. The binding compound of claim 1, wherein the binding compound is a humanized antibody comprising:
   a) a variable light chain sequence of SEQ ID NO: 70; and
   b) a variable heavy chain sequence of SEQ ID NO: 68.

7. The humanized antibody of claim 6, further comprising a heavy chain constant region comprising a γ1 human heavy chain constant region.

8. The humanized antibody of claim 6, further comprising a heavy chain constant region comprising a γ4 human heavy chain constant region.

* * * * *